US006348343B2

(12) United States Patent
Lazarus et al.

(10) Patent No.: US 6,348,343 B2
(45) Date of Patent: Feb. 19, 2002

(54) HUMAN DNASE I VARIANTS

(75) Inventors: Robert A. Lazarus, Millbrae; Steven Shak, Burlingame; Jana S. Ulmer, San Rafael, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/796,774

(22) Filed: Feb. 28, 2001

Related U.S. Application Data

(63) Continuation of application No. 08/929,995, filed on Sep. 15, 1997, now abandoned, which is a continuation of application No. 08/540,527, filed on Oct. 10, 1995, now abandoned, which is a continuation-in-part of application No. 08/403,873, and a continuation-in-part of application No. PCT/US95/02366, filed on Feb. 24, 1995, now abandoned.

(51) Int. Cl.$^7$ .......................... C12N 9/22; C12N 15/55; A61K 38/46

(52) U.S. Cl. ...................... 435/199; 424/94.6; 536/23.2

(58) Field of Search ...................... 435/194; 424/94.6; 536/23.2

(56) References Cited

FOREIGN PATENT DOCUMENTS

| WO | WO 90/07572 | 7/1990 |
|----|-------------|--------|
| WO | WO 93/25670 | 12/1993 |
| WO | WO 94/10567 | 5/1994 |
| WO | WO 94/22465 | 10/1994 |

OTHER PUBLICATIONS

Aitken et al., "Recombinant Human DNase Inhalation in Normal Subjects and Patients With Cystic Fibrosis" *Journal of the American Medical Assn.* 267 (14):1947–1951 (1992).
Bryson et al., "Dornase Alfa: A Review of its Pharmacological Properties and Therapeutic Potential in Cystic Fibrosis" *Drugs* 48 (6):894–906 (1994).
Doherty et al., "Mutagenesis of the DNA Binding Residues in Bovine Pancreatic DNase1: an Investigation Into the Mechanism of Sequence Discrimination by a Sequence Selective Nuclease" *Nucleic Acids Research* 19 (22):6129–6132 (1991).
Drummond et al., "The binding of mutant actins to profilin, ATP and DNase I" *European Journal of Biochemistry* 209:171–179 (1992).
Fitch et al., "Optimal Sequence Alignments" *Proc. Natl. Acad. Sci. USA* 80:1382–1386 (Mar. 1983).
Fuchs et al., "Effect of Aerosolized Recombinant Human DNase on Exacerbations of Respiratory Symptoms and on Pulmonary Function in Patients with Cystic Fibrosis" *New England J. of Medicine* 331(10):637–642 (1994).
Goldschmidt–Clermont et al., "Distinct Sites on the G–actin Molecule Bind Group–specific Component and Deoxyribonuclease I" *Biochemical Journal* 225:471–477 (1985).
Hitchcock et al., "Depolymerization on F–actin by Deoxyribonuclease I" *Cell* 7:531–542 (Apr. 1976).
Houmeida et al., "Localization of a Vitamin–D–binding Protein Interaction Site in the COOH–terminal Sequence of Actin" *European Journal of Biochemistry* 203:499–503 (1992).
Hubbard et al., "A Preliminary Study of Aerosolized Recombinant Human Deoxyribonuclease I in the Treatment of Cystic Fibrosis" *New England J. of Medicine* 326 (12):812–815 (Mar. 19, 1992).
Jamney, P., "A Torsion Pendulum for Measurement of the Viscoelasticity of Biopolymers and Its Application to Actin Networks" *J. Biochem. Biophys. Methods* 22:41–53 (1991).
Janmey et al., "Viscoelasticity of F–Actin and F–Actin/Gelsolin Complexes" *Biochemistry* 27:8218–8226 (1988).
Kabsch et al., "Atomic Structure of the Actin: DNase I Complex" *Nature* 347:37–44 (1990).
Kabsch et al., "Structure and Function of Actin" *Ann. Rev. Biophys. Biomol. Struct.*, Engelman et al. vol. 21:49–76 (1992).
Kreuder et al., "Isolation, Characterisation and Crystallization of Deoxyribonuclease I from Bovine and Rat parotid Gland and It's Interaction With Rabbit Skeletal Muscle Actin" *European Journal of Biochemistry* 139:389–400 (1984).
Kunitz, M., "Crystalline Desoxyribonuclease: I. Isolation and General Properties" *J. Gen. Physiol.*33:349–362 (1950).
Kunitz, M., "Crystalline Desoxyribonuclease: II. Digestion of Thymus Nucleic Acid (Desoxyribonucleic Acid)" *J. Gen. Physiol.*33:363–377 (1950).
Kurnick, N. B., "The Determination of Desoxyribonuclease Activity by Methyl Green; Application to Serum" *Arch. Biochem.*29:41–53 (1950).
Lacks, "Deoxyribonuclease I in mammalian tissues: Specificity of inhibition by actin" *Journal of Biological Chemistry* 256 (6):2644–2648 (1981).
Lacks, S., "Deoxyribonuclease I in Mammalian Tissues" *Journal of Biological Chemistry* 256 (6):2644–2648 (1981).
Lahm et al., "DNase I–induced DNA Conformation" *Journal Molecular Biology* 221:645–667 (1991).
Lazarides et al., "actin is the Naturally Occurring Inhibitor of Deoxyribonuclease I " *Proc. Natl. Acad. Sci. USA* 71 (12):4742–4746 (Dec. 1974).
Liao et al., "Bovine Pancreatic Deoxyribonuclease A" *Journal of Biological Chemistry* 248 (4):1489–1495 (1973).
Lourenco et al., "Clinical Aerosols. II. Therapeutic Aerosols" *Arch. Intern. Med.*142:2299–2308 (Dec. 1982).

(List continued on next page.)

*Primary Examiner*—Charles L. Patterson, Jr.
(74) *Attorney, Agent, or Firm*—David W. Evans

(57) ABSTRACT

The present invention relates to amino acid sequence variants of human DNase I that have reduced binding affinity for actin. The invention provides nucleic acid sequences encoding such actin-resistant variants, thereby enabling the production of these variants in quantities sufficient for clinical use. The invention also relates to pharmaceutical compositions and therapeutic uses of actin-resistant variants of human DNase I.

21 Claims, 13 Drawing Sheets

OTHER PUBLICATIONS

Mannherz et al., "A Specific 1:1 G–Actin:DNAse I Complex Formed by the Action of DNase I on F–Actin" *FEBS Letter* 60(1):34–38 (Dec. 1975).

Mannherz et al., "The Inhibition of Bovine and Rat Parotid Deoxyribnuclease I by Skeletal Muscle Actin" *Biochemical Journal* 207:305–313 (1982).

Mannherz et al., "The Interaction of Bovine Pancreatic Deoxyribonuclease I and Skeletal Muscle Actin" *European Journal of Biochemistry* 104:367–379 (1980).

Matsudaira et al., "Pieces in the Actin–severing Protein Puzzle" *Cell* 54:139–140 (Jul. 1988).

McLeod et al., "Interactions among Serum Vitamin D Binding Protein, Monomeric Actin, Profilin, and Profilactin" *Journal of Biological Chemistry* 264(2):1260–1267 (Jan. 1989).

Moore, S., "Pancreatic DNase" *The Enzymes*, Boyer, Ph. D., New York, NY:Academic Press vol. XIV:281–296 (1981).

Mornet et al., "Proteolysis and Structure of Skeletal Muscle Actin" *Proc. Natl. Acad. Sci. USA* 81:3680–3684 (Jun. 1984).

Needleman et al., "A General Method Applicable to the Search for Similarities in the Amino Acid Sequence of Two Proteins" *J. Mol. Biol.* 48:443–453 (1970).

Newman et al., "Presence of Oligomers at Subcritical Actin Concentrations" *Biochemistry* 24:1538–1544 (1985).

Ngo et al., "Computational Complexity, Protein Structure Prediction, and the Levinthal Paradox" *The Protein Folding Problem and Tertiary Structure Prediction*, Merz & Le Grand, Boston:Birkhauser pp. 491–495 (1994).

"Nucleotide sequence of a full length cDNA clone encoding the deoxyribonuclease I of the rat parotid gland" *Nucleic Acid Research* 18(23):7151 (1990).

Oefner et al., "Crystallographic Refinement and Structure of DNase I at 2 A Resolution" *Journal Molecular Biology* 192:605–632 (1986).

Pardee et al., "Purification of Muscle Actin" *Methods in Enzymology* 85:164–181 (1982).

Pinder et al., "Investigation of the Actin–Deoxyribonuclease I Interaction Using a Pyrene–conjugate Actin Derivative" *Biochemistry* 21:4886–4890 (1982).

Podolski et al., "Association of Deoxyribonuclease I with the Pointed Ends of Actin Filaments in Human Red Blood Cell Membrane Skeletons" *Journal of Biological Chemistry* 263 (2):638–645 (Jan. 15, 1988).

Ranasinha et al., "Efficacy and Safety of Short–term Administration of Aerosolised Recombinant Human DNase I in Adults with Stable Stage Cystic Fibrosis" *Lancet* 342 (8865):199–202 (Jul. 24, 1993).

Rudinger, J., "Characteristics of the Amino Acids as Components of a Peptide Hormone Sequence" *Peptide Hormones*, J.A. Parsons, Baltimore:University Park Press pp. 1–7 (1976).

Shak et al., "Recombinant Human DNase I Reduces the Viscosity of Cystic Fibrosis Sputum" *Proc. Natl. Acad. Sci. USA* 87 (23) :9188–9192 (Dec. 1990).

Sheterline et al. *Prot. Profile* 1:1–121 (1994).

Sinicropi et al., "Colorimetric Determination of DNase I Activity with a DNA–Methyl Green Substrate" *Analytical Biochemistry* 222:351–358 (1994).

Suck et al., "Structure of DNase I at 2.0 A Resolution Suggests a Mechanism for Binding To and Cutting DNA" *Nature* 321:620–625 (Jun. 1986).

Suck et al., "Structure refined to 2A of a Nicked DNA Octanucleotide Complex with DNase I " *Nature* 332:464–468 (1988).

Suck et al., "Three–dimensional Structure of Bovine Pancreatic DNase I at 2.5 A Resolution" *EMBO Journal* 3(10):2423–2430 (1984).

Thornton et al., "Protein Engineering: Editorial Overview" *Current Opinion in Biotechnology* 6(4):367–369 (1995).

Vasconcellos et al., "Reduction in Viscosity of Cystic Fibrosis Sputum in Vitro by Gelsolin" *Science* 263:969–971 (Feb. 1994).

Wallace, "Understanding cytochrome c function: engineering protein structure by semisynthesis" *The FASEB Journal* 7:505–515 (1993).

Weber et al., "DNase I Increases the Rate Constant of Depolymerization at the Pointed (–) End of Actin Filaments" *Biochemistry* 33(16):4780–4786 (1994).

Weston and Suck, "X–ray Structures of Two Single–Residue Mutants of DNase I: H134Q and Y76A " *Protein Engineering* 6(4):349–357 (1993).

Weston et al., "X–ray Structure of the DNase I–d (GGTATACC)2 Complex at 2.3 A Resolution" *J. Mol. Biol.* 226:1237–1256 (1992).

Worrall et al., "The Chemical Synthesis of a Gene Coding for Bovine Pancreatic DNase I and Its Cloning and Expression in *Escherichia coli*" *Journal Biological Chemistry* 265(35):21889–21895 (Dec. 1990).

```
        10         20         30         40         50
LKIAAFNIQTFGETKMSNATLVSYIVQILSRYDIALVQEVRDSHLTAVGK 60         70         80         90        100
LLDNLNQDAPDTYHYVVSEPLGRNSYKERYLFVYRPDQVSAVDSYYYDDG 110        120        130        140        150
CEPCGNDTFNREPAIVRFFSRFTEVREFAIVPLHAAPGDAVAEIDALYDV 160        170        180        190        200
YLDVQEKWGLEDVMLMGDFNAGCSYVRPSQWSSIRLWTSPTFQWLIPDSA 210        220        230        240        250
DTTATPTHCAYDRIVVAGMLLRGAVVPDSALPFNFQAAYGLSDQLAQAIS

260
DHYPVEVMLK
```

FIG. 1

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 260 amino acids
      (B) TYPE: Amino Acid
      (D) TOPOLOGY: Linear (xi) SEQUENCE DESCRIPTION: SEQ ID NO: 1:

```
Leu Lys Ile Ala Ala Phe Asn Ile Gln Thr Phe Gly Glu Thr Lys
 1               5                  10                  15

Met Ser Asn Ala Thr Leu Val Ser Tyr Ile Val Gln Ile Leu Ser
                20                  25                  30

Arg Tyr Asp Ile Ala Leu Val Gln Glu Val Arg Asp Ser His Leu
                35                  40                  45

Thr Ala Val Gly Lys Leu Leu Asp Asn Leu Asn Gln Asp Ala Pro
                50                  55                  60

Asp Thr Tyr His Tyr Val Val Ser Glu Pro Leu Gly Arg Asn Ser
                65                  70                  75

Tyr Lys Glu Arg Tyr Leu Phe Val Tyr Arg Pro Asp Gln Val Ser
                80                  85                  90

Ala Val Asp Ser Tyr Tyr Tyr Asp Asp Gly Cys Glu Pro Cys Gly
                95                 100                 105

Asn Asp Thr Phe Asn Arg Glu Pro Ala Ile Val Arg Phe Phe Ser
               110                 115                 120

Arg Phe Thr Glu Val Arg Glu Phe Ala Ile Val Pro Leu His Ala
               125                 130                 135

Ala Pro Gly Asp Ala Val Ala Glu Ile Asp Ala Leu Tyr Asp Val
               140                 145                 150

Tyr Leu Asp Val Gln Glu Lys Trp Gly Leu Glu Asp Val Met Leu
               155                 160                 165

Met Gly Asp Phe Asn Ala Gly Cys Ser Tyr Val Arg Pro Ser Gln
               170                 175                 180

Trp Ser Ser Ile Arg Leu Trp Thr Ser Pro Thr Phe Gln Trp Leu
               185                 190                 195

Ile Pro Asp Ser Ala Asp Thr Thr Ala Thr Pro Thr His Cys Ala
               200                 205                 210

Tyr Asp Arg Ile Val Val Ala Gly Met Leu Leu Arg Gly Ala Val
               215                 220                 225

Val Pro Asp Ser Ala Leu Pro Phe Asn Phe Gln Ala Ala Tyr Gly
               230                 235                 240

Leu Ser Asp Gln Leu Ala Gln Ala Ile Ser Asp His Tyr Pro Val
               245                 250                 255

Glu Val Met Leu Lys
               260
```

HUMAN DNASE I VARIANTS

This is a continuation of application(s) Ser. No. 08/929,995, filed on Sep. 15, 1997, now abandoned which is a continuation of application Ser. No.08/540,527, filed on Oct. 10, 1995, now abandoned, which is a continuation-in-part of application Ser. No. 08/403.873, filed on Mar. 24, 1995, now abandoned, which applications are incorporated herein by reference and to which applications priority is claimed under 35 USC §120. International Application PCT/US95/02366, filed on Feb. 24, 1995, which designated the U.S., which application is incorporated herein by reference and to which application priority is claimed under 35 USC §120.

FIELD OF THE INVENTION

The present invention is related to results obtained from research on human deoxyribonuclease I (DNase I), a phosphodiesterase that is capable of hydrolyzing polydeoxyribonucleic acid. It relates generally to modified (variant) forms of human DNase I and their preparation by recombinant DNA methods, to pharmaceutical compositions by which their utility can be exploited clinically, and to methods of using these DNase I variants and compositions thereof.

BACKGROUND OF THE INVENTION

DNase I is a phosphodiesterase capable of hydrolyzing polydeoxyribonucleic acid. DNase I has been purified from various species to various degrees.

Bovine DNase I has been extensively studied biochemically. See e.g., Moore, in *The Enzymes* (Boyer, P. D., ed), pp. 281–296, Academic press, New York (1981). The complete amino acid sequence for bovine DNase I is known (Liao, et al., J. Biol. Chem. 248:1489–1495 (1973); Oefner, et al., J. Mol. Biol. 192:605–632 (1986); Lahm, et al., J. Mol. Biol. 221:645–667 (1991)), and DNA encoding bovine DNase I has been cloned and expressed (Worrall, et al., J. Biol. Chem 265:21889–21895 (1990)). The structure of bovine DNase I has been determined by X-ray crystallography. Suck, et al., EMBO J. 3:2423–2430 (1984); Suck, et al., Nature 321:620–625 (1986); Oefner, et al., J. Mol. Biol. 192:605–632 (1986).

DNA encoding human DNase I has been isolated and sequenced and that DNA has been expressed in recombinant host cells, thereby enabling the production of human DNase I in commercially useful quantities. Shak, et al., Proc. Nat. Acad. Sci. 87:9188–9192 (1990).

DNase I has a number of known utilities and has been used for therapeutic purposes. Its principal therapeutic use has been to reduce the viscoelasticity of pulmonary secretions (mucus) in such diseases as pneumonia and cystic fibrosis (CF), thereby aiding in the clearing of respiratory airways. See e.g., Lourenco, et al., Arch. Intern. Med. 142:2299–2308 (1982); Shak, et al., Proc. Nat. Acad. Sci. 87:9188–9192 (1990); Hubbard, et al., New Engl. J. Med. 326:812–815 (1992); Fuchs, et al., New Engl. J. Med. 331:637–642 (1994); Bryson, et al., Drugs 48:894–906 (1994). Mucus also contributes to the morbidity of chronic bronchitis, asthmatic bronchitis, bronchiectasis, emphysema, acute and chronic sinusitis, and even the common cold.

The pulmonary secretions of persons having such diseases are complex materials, that include mucus glycoproteins, mucopolysaccharides, proteases, actin, and DNA. Some of the materials in pulmonary secretions are released from leukocytes (neutrophils) that infiltrate pulmonary tissue in response to the presence of microbes (e.g., strains of Pseudomonas, Pneumococcus, or Staphylococcus bacteria) or other irritants (e.g., tobacco smoke, pollen). In the course of reacting with such microbes or irritants, the leukocytes may degenerate and release their contents, which contribute to the viscoelasticity of the pulmonary secretions.

The ability of DNase I to reduce the viscoelasticity of pulmonary secretions has been ascribed to its enzymatic degradation of the large amounts of DNA released by neutrophils. Shak, et al., Proc. Nat. Acad. Sci. 87:9188–9192 (1990); Aitken, et al., J. Am. Med. Assoc. 267:1947–1951 (1992).

More recently, a different mechanism has been proposed for the mucolytic effect of DNase I, involving disaggregation of actin. Vasconcellos, et al., Science 263:969–971 (1994). Actin is one of the most abundant proteins in eukaryotic cells (for example, actin comprises about 10% of total leukocyte protein) and has been extensively studied. Kabsch, et al., Ann. Rev. Biophys. Biomol. Struct. 21:49–76 (1992); Sheterline, et al., Prot. Profile 1:1–121 (1994). Actin exists in two forms, a monomeric form (G-actin), and a filamentous form (F-actin) that is assembled from G-actin monomers. Polymeric filaments of actin are highly viscoelastic and contribute significantly to the viscosity of pulmonary secretions. Mornet, et al., Proc. Nat. Acad. Sci. 81:3680–3684 (1984); Newman, et al., Biochemistry 24:1538–1544 (1985); Janmey, et al., Biochemistry 27:8218–8226 (1988); Vasconcellos, et al., Science 263:969–971 (1994).

Because DNase I is known to bind to actin (Lazarides, et al., Proc. Nat. Acad. Sci. 71:4742–4746 (1974); Kabsch, et al., Nature 347:37–44 (1990)) and to depolymerize actin filaments (as well as inhibit polymerization of G-actin into filaments) (Mannherz, et al., FEBS Lett. 60:34–38 (1975); Hitchcock, et al., Cell 7:531–542 (1976); Pinder, et al., Biochemistry 21:4886–4890 (1982); Weber, et al., Biochemistry 33:4780–4786 (1994)), it has been suggested that the mucolytic effect of DNase I on sputum and other pulmonary secretions is due to actin disaggregation (depolymerization) rather than to DNA hydrolysis. Vasconcellos, et al., Science 263:969–971 (1994). Consistent with this view, it is known that in the presence of actin, the DNA-hydrolytic activity of DNase I is inhibited. Lazarides, et al., Proc. Nat. Acad. Sci. 71:4742–4746 (1974); Mannherz, et al., Eur. J. Biochem. 104:367–379 (1980). Also consistent with this view, it has been reported that actin severing proteins (e.g., gelsolin) are effective in decreasing the viscoelasticity of cystic fibrosis sputum. Vasconcellos, et al., Science 263:969–971 (1994); Stossel, et al., PCT Patent Publication No. WO 94/22465 (published Oct. 13, 1994).

The present invention is based in part on research by the inventors to determine the biochemical basis of the mucolytic activity of DNase I. This research involved the design and synthesis of various human DNase I variants, and the assay of these variants to assess their ability to hydrolyze DNA, to bind to actin, and to reduce the viscoelasticity of sputum in vitro. The inventors created several classes of human DNase I variants. One class of variants (actin-resistant variants) has decreased ability to bind actin, but still has mucolytic activity and in some cases had increased mucolytic activity as compared to native human DNase I. These actin-resistant variants have about the same DNA-hydrolytic activity as native human DNase I, but such activity is less susceptible to inhibition by actin. A second class of variants bind actin with an affinity similar to that found for native human DNase I, but have decreased mucolytic activity and decreased DNA-hydrolytic activity as compared to native human DNase I.

These results indicate that the therapeutic efficacy of human DNase I in reducing the viscoelasticity of pulmonary secretions is due to its catalytic, DNA-hydrolytic activity, rather than to its ability to depolymerize filamentous actin. Accordingly, variants of human DNase I that bind actin with lower affinity than native human DNase I, but that still possess DNA-hydrolytic activity should be useful therapeutic agents, especially in the treatment of patients having pulmonary secretions that comprise relatively large amounts of actin. Because such variants have reduced affinity for actin, their DNA hydrolytic activity is less inhibited in the presence of actin, and so these variants have greater mucolytic activity in the presence of actin, as compared to native human DNase I.

It is therefore an object of the present invention to provide human DNase I variants that possess DNA-hydrolytic activity, but bind actin with lower affinity than native human DNase I.

It is another object of the invention to provide nucleic acids encoding such actin-resistant variants of human DNase I, recombinant vectors comprising such nucleic acids, recombinant host cells transformed with those nucleic acids or vectors, and processes for producing the human DNase I variants by means of recombinant DNA technology.

The invention also is directed to pharmaceutical compositions comprising the human DNase I actin-resistant variants, optionally together with a pharmaceutically acceptable excipient.

The invention also is directed to a method for reducing the viscoelasticity or viscous consistency of DNA-containing material in a patient, comprising administering a therapeutically effective dose of an actin-resistant variant of DNase I to the patient.

The invention is particularly directed to a method of treating a patient having a disease such as cystic fibrosis, chronic bronchitis, pneumonia, bronchiectasis, emphysema, asthma, or systemic lupus erythematosus, that comprises administering a therapeutically effective amount of an actin-resistant variant of DNase I to the patient.

The invention also is directed to the use of actin-resistant variants of human DNase I in in vitro diagnostic assays of a viscous material (e.g., sputum) from a patient, to measure the amount of actin present and determine whether the patient is an appropriate candidate for treatment with an actin-resistant DNase I variant.

These and other objects of the invention will be apparent to the ordinary artisan upon consideration of the specification as a whole.

BRIEF DESCRIPTION OF THE FIGURES

FIG. 1 shows the amino acid sequence of human mature DNase I (SEQ. ID. NO: 1). The numbers indicate the sequential position of amino acid residues within the sequence.

DETAILED DESCRIPTION

I. Definitions

As used herein, the terms "human DNase I", "native human DNase I", and "wild-type DNase I" refer to the polypeptide having the amino acid sequence of human mature DNase I set forth in FIG. 1.

A "variant" or "amino acid sequence variant" of human DNase I is a polypeptide that comprises an amino acid sequence different from that of native human DNase I. Generally, a variant will possess at least 80% sequence identity (homology), preferably at least 90% sequence identity, more preferably at least 95% sequence identity, and most preferably at least 98% sequence identity with native human DNase I. Percentage sequence identity is determined, for example, by the Fitch, et al., Proc. Nat. Acad. Sci. USA 80:1382–1386 (1983), version of the algorithm described by Needleman, et al., J. Mol. Biol. 48:443–453 (1970), after aligning the sequences to provide for maximum homology.

The terms "human DNase I actin-resistant variant", "actin-resistant variant", and "actin-resistant variant of human DNase I" refer to a variant of native human DNase I that has (1) DNA-hydrolytic activity and (2) reduced binding affinity for actin.

"DNA-hydrolytic activity" refers to the enzymatic activity of native human DNase I or a variant of human DNase I in hydrolyzing (cleaving) substrate DNA to yield 5'-phosphorylated oligonucleotide end products. DNA-hydrolytic activity is readily determined by any of several different methods known in the art, including analytical polyacrylamide and agarose gel electrophoresis, hyperchromicity assay (Kunitz, J. Gen. Physiol. 33:349–362 (1950); Kunitz, J. Gen. Physiol. 33:363–377 (1950)), or methyl green assay (Kurnick, Arch. Biochem. 29:41–53 (1950); Sinicropi, et al., Anal. Biochem. 222:351–358 (1994)).

The "binding affinity" of native human DNase I or an actin-resistant variant of human DNase I for actin refers to the ability of the DNase I to noncovalently bind to actin. Binding affinity may be determined by any of various methods known in the art, for example, as described in Mannherz, et al., Eur. J. Biochem. 104:367–379 (1980). Alternatively, the relative binding affinities of different DNases (e.g., native human DNase I and variants thereof) are determined by measuring the binding of the DNases to immobilized actin in an ELISA assay (described in Example 3), or by comparing the DNA-hydrolytic activity of the DNases in the presence and absence of actin (also described in Example 3). The methods described in the Examples are especially convenient for screening variants of human DNase I to rapidly identify those variants that have a reduced binding affinity for actin.

Figure 5A:
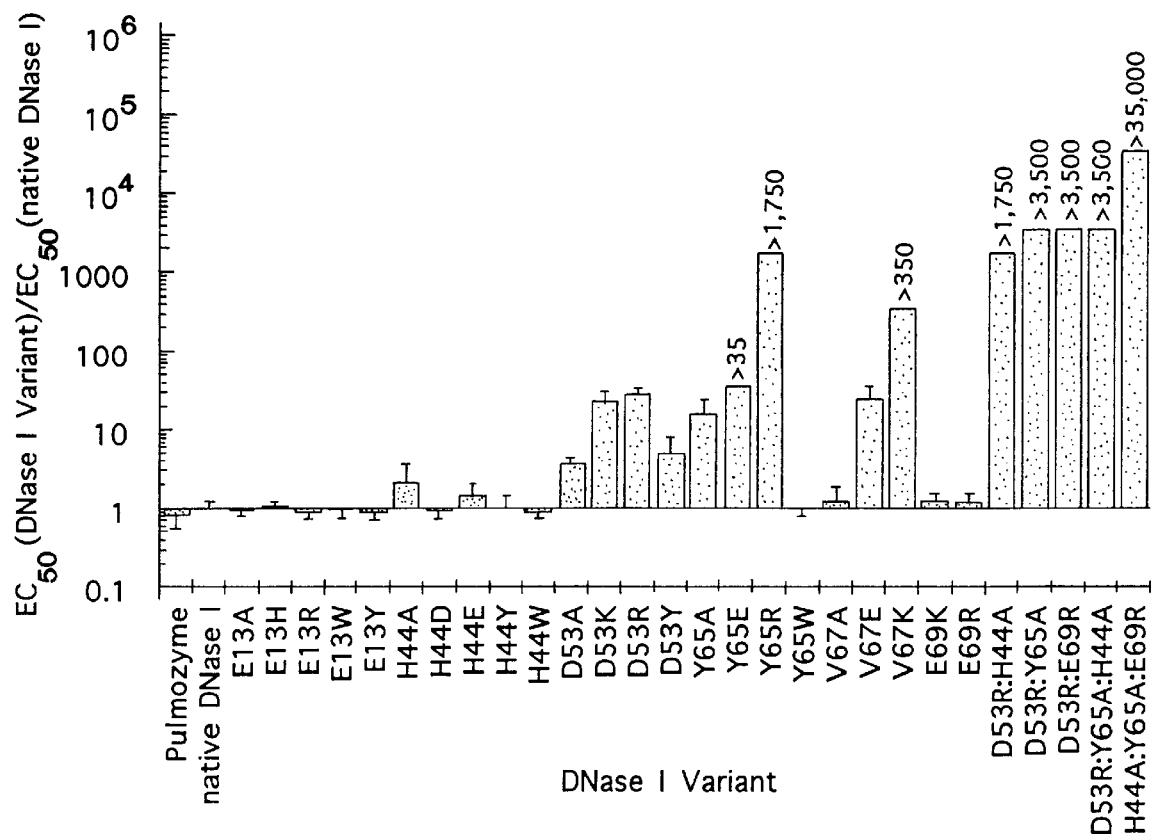
FIGS. 5A–D show the relative binding affinity of human DNase I variants for actin as determined in an actin binding ELISA assay (as described in Example 3). The $EC_{50}$ value is the concentration of the DNase I (native or variant) that is required to give a half-maximal signal in the assay. The error bars represent the standard deviation. The $EC_{50}$ values for Pulmozyme® and native human DNase I are 67±23 pM (n=31) and 87±14 pM (n=32), respectively. The relative binding affinity shown in the figure is the $EC_{50}$ value determined for the human DNase I variant divided by the $EC_{50}$ value determined for native human DNase I. Variants where the $EC_{50}$ value was larger than could be measured in the assay are indicated as having a ratio ($EC_{50}$ (DNase I variant)/$EC_{50}$ (native DNase I)) greater than a certain value (for example, <10, <100, <300, <2000, <20,000, <35,000).
Figure 5B:
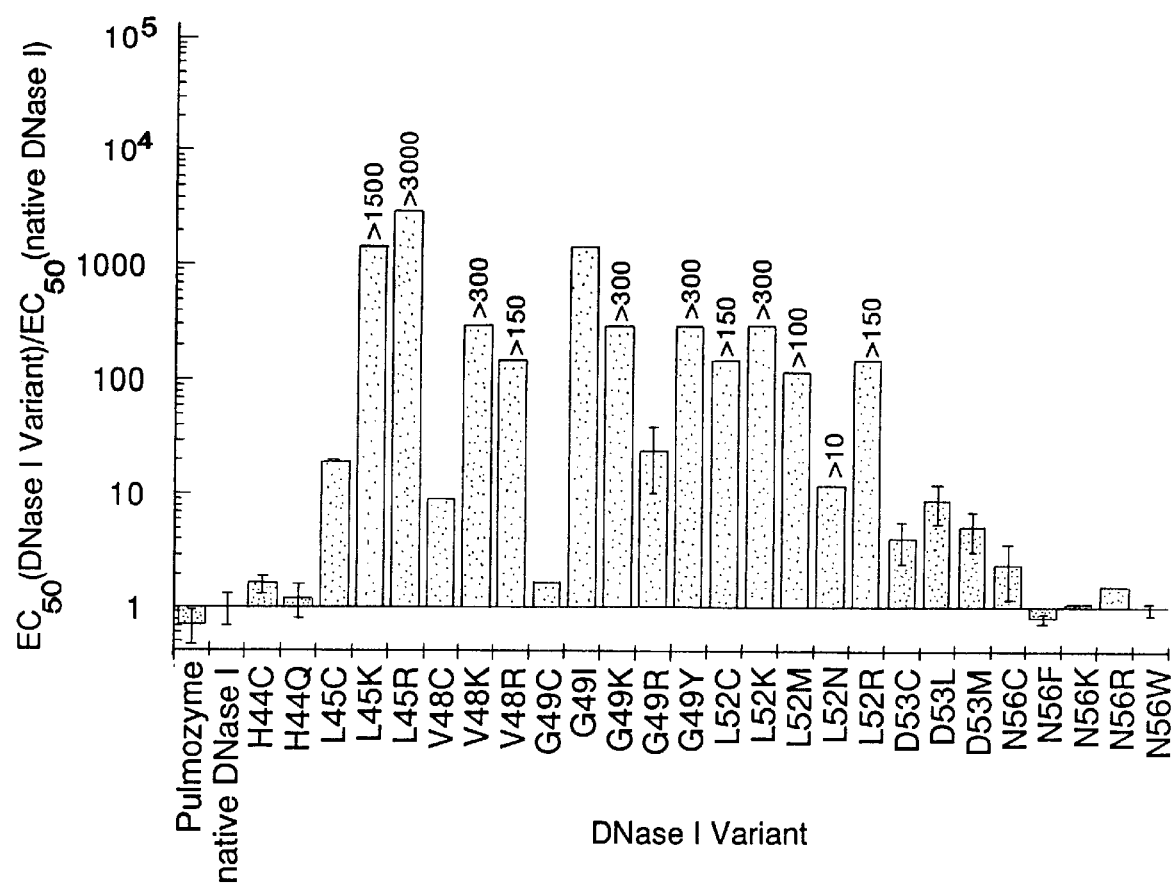
Figure 5C:
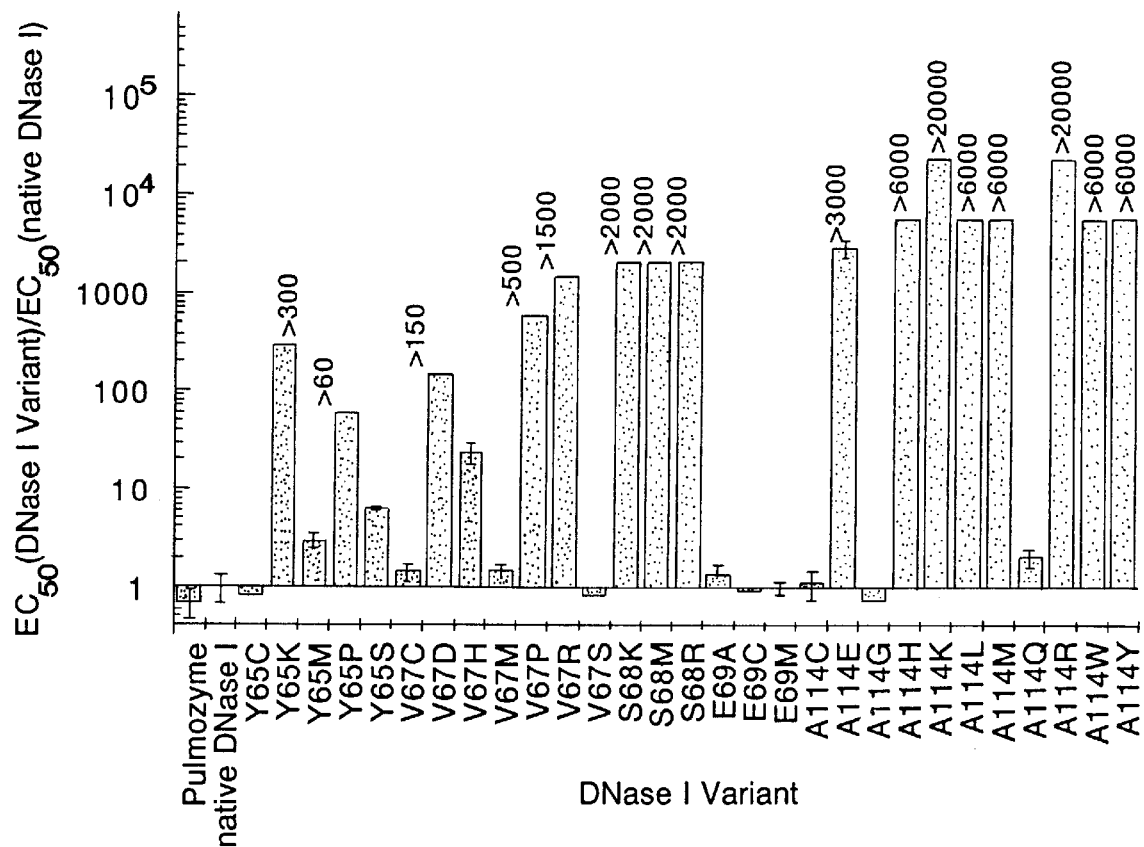
Figure 5D:
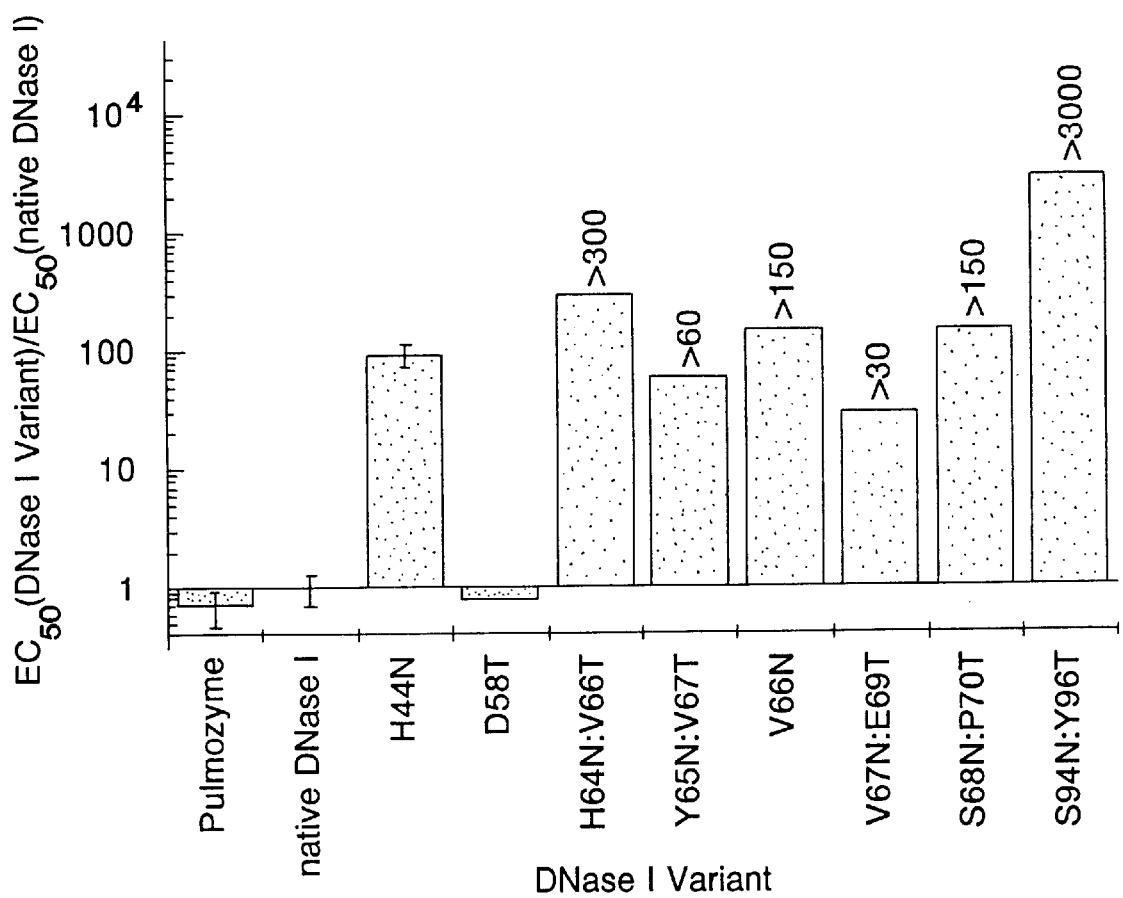

A human DNase I actin-resistant variant having "reduced binding affinity for actin" is one having a binding affinity for actin that is relatively less than the affinity with which native human DNase I binds actin, determined under comparable conditions. If the actin binding ELISA assay as described in Example 3 is used to determine the binding affinity of a human DNase I (native or variant) for actin, then an actin-resistant variant having "reduced binding affinity for actin" will be one having an $EC_{50}$ value that is greater than that of native human DNase I. In that assay, an actin-resistant variant typically will have an $EC_{50}$ value five-fold to 100-fold greater than that of native human DNase; but actin-resistant variants having an $EC_{50}$ value over 500-fold greater than that of native human DNase I also are readily produced, especially by altering multiple amino acid residues of the native human DNase I amino acid sequence (see e.g., FIG. 5A, 5D).

"Mucolytic activity" refers to the reduction of viscoelasticity (viscosity) of sputum or other biological material, for example as observed upon treatment of the material with native human DNase I or a variant of human DNase I. Mucolytic activity is readily determined by any of several different methods known in the art, including sputum compaction assay (PCT Patent Publication No. WO 94/10567, published May 11, 1994), assays using a torsion pendulum (Janmey, J. Biochem. Biophys. Methods 22:41–53 (1991), or other rheological methodologies.

"Polymerase chain reaction," or "PCR," generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridizing preferentially to a template nucleic acid.

"Cell," "host cell," "cell line," and "cell culture" are used interchangeably herein and all such terms should be understood to include progeny resulting from growth or culturing of a cell. "Transformation" and "transfection" are used interchangeably to refer to the process of introducing DNA into a cell.

"Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Amino acids are identified herein by three-letter or single-letter designations, as follows:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

II. Selection of Actin-Resistant Variants

The present invention is based upon the study of structure, actin binding properties, DNA-hydrolytic activity, and mucolytic activity of amino acid sequence variants of human DNase I. The actin-resistant variants of the present invention have DNA-hydrolytic activity, but bind actin with less affinity than native human DNase I. The reduction in actin binding preferably is achieved by making mutations at and/or around those amino acid residues within native human DNase I that appear to affect the binding of actin, including, for example, the Glu13, His44, Leu45, Val48, Gly49, Leu52, Asp53, AsnS6, Asp58, His64, Tyr65, Val66, Val67, Ser68, Glu69, Pro70, Ser94, Tyr96, and Ala114 residues of native human DNase I (the number following the three-letter amino acid designation indicates the specific position of the amino acid residue within the FIG. 1 sequence).

There are a variety of ways in which one can make actin-resistant variants of human DNase I. In one embodiment of this invention, an actin-resistant variant is prepared by introducing either single or multiple amino acid substitutions, insertions, and/or deletions at or adjacent to (i.e., within about five amino acid residues of) those amino acid residues of native human DNase I that affect actin binding. Some illustrative examples of such mutations are as follows: D53R, D53K, D53Y, D53A, Y65A, Y65E, Y65R, V67E, V67K, E69R, D53R:Y65A, D53R:E69R, H44A:D53R:Y65A, H44A:Y65A:E69R (see FIGS. 2–6

In another embodiment of this invention, an actin-resistant variant is prepared by introducing mutation(s) that create a new glycosylation site at or adjacent to (i.e., within about five amino acid residues of) an amino acid residues of native human DNase I that affect actin binding. For example, site-directed mutagenesis is used to introduce one of the tripeptide sequences, asparagine-X-serine or asparagine-X-threonine (wherein X is any amino acid except proline), which are recognition sequences for enzymatic attachment of a carbohydrate moiety to the asparagine side chain. Creighton, *Proteins*, pp.76–78 (W. H. Freeman, 1984). Steric hindrance occurring between the carbohydrate moiety of the resulting N-glycosylated variant DNase I and actin can reduce or prevent actin binding and consequential inhibition of the DNase I DNA-hydrolytic activity, as compared to native human DNase I. Some illustrative examples of such mutations to introduce a new glycosylation site are as follows: H44N, D58S, D58T, V66N, H44N:T46S, H64N:V66S, H64N:V66T, Y65N:V67S, Y65N:V67T, V66N:S68T, V67N:E69S, V67N:E69T, S68N:P70S, S68N:P70T, S94N:Y96S, S94N:Y96T.

Optionally, in conjunction with such mutations to create a new glycosylation site, the naturally occurring glycosylation site at positions 18 and/or 106 within the native human DNase I amino acid sequence may be deleted, depending upon the extent of glycosylation desired in the actin-resistant variant.

In a further embodiment of this invention, site-directed mutagenesis is used to introduce residues at or adjacent to (i.e., within about five amino acid residues of) those amino acid residues of native human DNase I that are involved in actin binding that are suitable for post-translational modification either biologically or chemically (see below). Means, et al., *Chemical Modification of Proteins* (Holden-Day, 1971); Glazer, et al., *Chemical Modification of Proteins: Selected Methods and Analytical Procedures* (Elsevier, 1975); Creighton, Proteins, pp.70–87 (W. H. Freeman, 1984); Lundblad, *Chemical Reagents for Protein Modification* (CRC Press, 1991). Such post-translational modifications may introduce steric hinderance or altered electrostatic properties into the DNase I that will reduce or prevent-actin binding and subsequent inhibition of DNA-hydrolytic activity, as compared to native human DNase I. For example, a cysteine residue may be introduced at or adjacent to a residue of native human DNase I that is involved in actin binding. The free thiol of the cysteine residue may form an intermolecular disulfide bond with another such DNase I variant to form a DNase I dimer, or may be modified, for example, with a thiol-specific alkylating agent. Some illustrative examples of such mutations are as follows: H44C, L45C, V48C, G49C, L52C, D53C, N56C, Y65C, V67C, E69C, A114C.

For convenience, substitutions, insertions, and/or deletions in the amino acid sequence of native human DNase I are usually made by introducing mutations into the corresponding nucleotide sequence of the DNA encoding native human DNase I, for example by site-directed mutagenesis. Expression of the mutated DNA then results in production of the variant human DNase I, having the desired (non-native) amino acid sequence.

Whereas any technique known in the art can be used to perform site-directed mutagenesis, e.g. as disclosed in Sambrook, et al., *Molecular Cloning: A Laboratory Manual*, Second Edition (Cold Spring Harbor Laboratory Press, New York (1989)), oligonucleotide-directed mutagenesis is the preferred method for preparing the human DNase I variants of this invention. This method, which is well known in the art (Zoller, et al., Meth. Enz. 100:4668–500 (1983); Zoller, et al., Meth. Enz. 154:329–350 (1987); Carter, Meth. Enz. 154:382–403 (1987); Kunkel, et al., Meth. Enzymol. 154:367–382 (1987); Horwitz, et al., Meth. Enz. 185:599–611 (1990)), is particularly suitable for making substitution variants, although it may also be used to conveniently prepare deletion and insertion variants.

The site-directed mutagenesis technique typically employs a phage vector that exists in both a single-stranded and double-stranded form. Typical vectors useful in site-directed mutagenesis include vectors such as the M13 phage, and plasmid vectors that contain a single-stranded phage origin of replication (Messing, et al., Meth. Enzymol. 101:20–78 (1983); Veira et al., Meth. Enzymol. 153:3–11 (1987); Short, et al., Nuc. Acids. Res. 16:7583–7600 (1988)). Replication of these vectors in suitable host cells results in the synthesis of single-stranded DNA that may be used for site-directed mutagenesis.

Briefly, in carrying out site-directed mutagenesis of DNA encoding native human DNase I (or a variant thereof), the DNA is altered by first hybridizing an oligonucleotide encoding the desired mutation to a single strand of the DNA. After hybridization, a DNA polymerase is used to synthesize an entire second strand, using the hybridized oligonucleotide as a primer, and using the single strand of the DNA as a template. Thus, the oligonucleotide encoding the desired mutation is incorporated in the resulting double-stranded DNA.

Oligonucleotides for use as hybridization probes or primers may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90–98 (1979); Brown, et al., Meth. Enzymol. 68:109–151 (1979); Caruthers, et al., Meth. Enzymol. 154:287–313 (1985). The general approach to selecting a suitable hybridization probe or primer is well known. Keller, et al., DNA Probes, pp.11–18 (Stockton Press, 1989). Typically, the hybridization probe or primer will contain 10–25 or more nucleotides, and will include at least 5 nucleotides on either side of the sequence encoding the desired mutation so as to ensure that the oligonucleotide will hybridize preferentially at the desired location to the single-stranded DNA template molecule.

Of course, site-directed mutagenesis may be used to introduce multiple substitution, insertion, or deletion mutations into a starting DNA. If the sites to be mutated are located close together, the mutations may be introduced simultaneously using a single oligonucleotide that encodes all of the desired mutations. If, however, the sites to be mutated are located some distance from each other (separated by more than about ten nucleotides), it is more difficult to generate a single oligonucleotide that encodes all of the desired changes. Instead, one of two alternative methods may be employed.

In the first method, a separate oligonucleotide is generated for each desired mutation. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired variant. The first round is as described for introducing a single mutation. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis (Higuchi, in *PCR Protocols*, pp.177–183 (Academic Press, 1990); Vallette, et al., Nuc. Acids Res. 17:723–733 (1989)) is also suitable for making the variants of human DNase I. Briefly, when small amounts of template DNA are used as starting material in a PCR, primers that differ slightly in sequence from the corresponding region in the template DNA can be used to generate relatively large quantities of a specific DNA fragment that differs from the template sequence only at the positions where the primers differ from the template. For introduction of a mutation into a plasmid DNA, for example, the sequence of one of the primers includes the desired mutation and is designed to hybridize to one strand of the plasmid DNA at the position of the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in PCR Topics, pp.69–71 (Springer-Verlag, 1991).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315–323 (1985). The starting material is the plasmid (or other vector) comprising the DNA sequence to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. The resulting plasmid contains the mutated DNA sequence.

The presence of mutation(s) in a DNA is determined by methods well known in the art, including restriction mapping and/or DNA sequencing. A preferred method for DNA sequencing is the dideoxy chain termination method of Sanger, et al., Proc. Nat. Acad. Sci. USA 72:3918–3921 (1979).

DNA encoding a human DNase I variant is inserted into a replicable vector for further cloning or expression. "Vectors" are plasmids and other DNAS that are capable of replicating within a host cell, and as such, are useful for performing two functions in conjunction with compatible host cells (a vector-host system). One function is to facilitate the cloning of the nucleic acid that encodes a human DNase I variant i.e., to produce usable quantities of the nucleic acid. The other function is to direct the expression of a human DNase I variant. One or both of these functions are performed by the vector in the particular host cell used for cloning or expression. The vectors will contain different components depending upon the function they are to perform.

To produce a human DNase I variant, an expression vector will comprise DNA encoding the variant, as described above, operably linked to a promoter and a ribosome binding site. The variant then is expressed directly in recombinant cell culture, or as a fusion with a heterologous polypeptide, preferably a signal sequence or other polypeptide having a specific cleavage site at the junction between the heterologous polypeptide and the human DNase I variant.

Prokaryotes (e.g., *E. coli*, and other bacteria) are the preferred host cells for the initial cloning steps of this invention. They are particularly useful for rapid production of large amounts of DNA, for production of single-stranded DNA templates used for site-directed mutagenesis, and for DNA sequencing of the variants generated. Prokaryotic host cells also may be used for expression of DNA encoding a human DNase I variant. Polypeptides that are produced in prokaryotic cells typically will be non-glycosylated.

In addition, the human DNase I variants of this invention may be expressed in eukaryotic host cells, including eukaryotic microbes (e.g., yeast) or cells derived from an animal or other multicellular organism (e.g., Chinese hamster ovary cells, and other mammalian cells), or in live animals (e.g., cows, goats, sheep)

Cloning and expression methodologies are well known in the art. Examples of prokaryotic and eukaryotic host cells, and expression vectors, suitable for use in producing the human DNase I variants of the present invention are, for example, those disclosed in Shak, PCT Patent Publication No. WO 90/07572 (published Jul. 12, 1990).

If prokaryotic cells or cells that contain substantial cell wall constructions are used as hosts, the preferred methods of transfection of the cells with DNA is the calcium treatment method described by Cohen et al., Proc. Natl. Acad. Sci. 69:2110–2114 (1972) or the polyethylene glycol method of Chung et al., Nuc. Acids. Res. 16:3580 (1988). If yeast are used as the host, transfection is generally accomplished using polyethylene glycol, as taught by Hinnen, *Proc. Natl. Acad. Sci.* U.S.A., 75: 1929–1933 (1978). If mammalian cells are used as host cells, transfection generally is carried out by the calcium phosphate precipitation method, Graham, et al., Virology 52:546 (1978), Gorman, et al., DNA and Protein Eng. Tech. 2:3–10 (1990). However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding human DNase I variants. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Wong, et al., Science 228:810–815 (1985); Lee, et al., Proc. Nat Acad. Sci. USA 82:4360–4364 (1985); Yang, et al., Cell 47:3–10 (1986). Thus, transient expression systems are conveniently used for expressing the DNA encoding amino acid sequence variants of native human DNase I, in conjunction with assays to identify those variants that bind actin with lower affinity than native human DNase I as well as assays to measure those variants with DNA-hydrolytic activity.

A human DNase I variant preferably is secreted from the host cell in which it is expressed, in which case the variant is recovered from the culture medium in which the host cells are grown. In that case, it may be desirable to grow the cells in a serum free culture medium, since the absence of serum proteins and other serum components in the medium may facilitate purification of the variant. If it is not secreted, then the human DNase I variant is recovered from lysates of the host cells. When the variant is expressed in a host cell other than one of human origin, the variant will be completely free of proteins of human origin. In any event, it will be necessary to purify the variant from recombinant cell proteins in order to obtain substantially homogeneous preparations of the human DNase I variant. For therapeutic uses, the purified variant preferably will be greater than 99% pure (i.e., any other proteins will comprise less than 1% of the total protein in the purified composition).

Generally, purification of a human DNase I variant is accomplished by taking advantage of the differential physicochemical properties of the variant as compared to the contaminants with which it may be associated. For example, as a first step, the culture medium or host cell lysate is centrifuged to remove particulate cell debris. The human DNase I variant thereafter is purified from contaminant soluble proteins and polypeptides, for example, by ammonium sulfate or ethanol precipitation, gel filtration (molecular exclusion chromatography), ion-exchange chromatography, hydrophobic chromatography, immunoaffinity chromatography (e.g., using a column comprising anti-human DNase I antibodies coupled to Sepharose), tentacle cation exchange chromatography (Frenz, et al., PCT Patent Publication No. WO 93/25670, published Dec. 23, 1993), reverse phase HPLC, and/or gel electrophoresis.

Of course, one skilled in the art will appreciate that the purification methods that are used for native human DNase I may require some modification to be useful in purifying a human DNase I variant, to account for structural and other differences between the native and variant proteins. For example, in some host cells (especially bacterial host cells) the human DNase I variant may be expressed initially in an insoluble, aggregated form (referred to in the art as "refractile bodies" or "inclusion bodies") in which case it will be necessary to solubilze and renature the human DNase I variant in the course of its purification. Methods for solubilizing and renaturing recombinant protein refractile bodies are known in the art (see e.g., Builder, et al., U.S. Pat. No. 4,511,502).

In another embodiment of this invention, human DNase I variants are prepared by making covalent modifications directly in a native or variant human DNase I protein. Such modifications are made to affect actin binding or another property of the protein (e.g., stability, biological half-life, immunogenicity), and may be made instead of or in addition to the amino acid sequence substitution, insertion, and deletion mutations described above.

Covalent modifications may be introduced by reacting targeted amino acid residues of the native or variant human DNase I with an organic derivatizing agent that is capable of reacting with selected amino acid side-chains or N- or C-terminal residues. Suitable derivatizing agents and methods are well known in the art.

For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $PK_a$ of the guanidine functional group. Furthermore, these reagents may react with the groups of lysine as well as the arginine epsilon-amino group.

Carboxyl side groups (aspartyl or glutamyl) are selectively modified by reaction with carbodiimides (R'—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Covalent coupling of glycosides to amino acid residues of the protein may be used to modify or increase the number or profile of carbohydrate substituents, especially at or adjacent to those residues that are involved in actin binding. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan or (f) the amide group of glutamine. Suitable methods are described, for example in PCT Patent Publication No. WO 87/05330 (published Sep. 11, 1987), and in Aplin, et al., CRC Crit. Rev. Biochem., pp. 259–306 (1981).

The covalent attachment of agents such as polyethylene glycol (PEG) or human serum albumin to human DNase I variants may reduce immunogenicity and/or toxicity of the variant and/or prolong its half-life, as has been observed with other proteins. Abuchowski, et al., J. Biol. Chem. 252:3582–3586 (1977); Poznansky, et al., FEBS Letters 239:18–22 (1988); Goodson, et al., Biotechnology 8:343–346 (1990); Katre, J. Immunol. 144:209–213 (1990); Harris, *Polyethylene Glycol Chemistry* (Plenum Press, 1992). In addition, modification of native human DNase I or a variant thereof by these agents at or adjacent to (i.e., within about five amino acid residues of) an amino acid residue that affects actin binding may result in an actin-resistant variant.

In a further embodiment, a human DNase I actin-resistant variant may comprise a mutation at the Asn residue that occurs at position 74 of the native human DNase I amino acid sequence (e.g., a N74D, N74K, or N74S mutation), in order to reduce or prevent the deamidation of the DNase I variant. Frenz, et al., PCT Patent Publication No. WO 93/25670, published Dec. 23, 1993. As another example, a human DNase I actin-resistant variant may comprise an amino acid sequence mutation or other covalent modification that reduces the susceptibility of the variant to degradation by proteases (e.g., neutrophil elastase) that may be present in sputum and other biological materials.

The DNA-hydrolytic activity and actin-binding affinity of the human DNase I variants prepared as described above are readily determined using assays and methods known in the art and as described herein. Any such variant having DNA-hydrolytic activity and reduced binding affinity for actin (as defined above) is an actin-resistant variant within the scope of this invention.

The human DNase I actin-resistant variants of this invention are used to reduce the viscoelasticity of DNA-containing material, such as sputum, mucus, or other pulmonary secretions. Such variants are particularly useful for the treatment of patients with pulmonary disease who have abnormal viscous or inspissated secretions and conditions such as acute or chronic bronchial pulmonary disease, including infectious pneumonia, bronchitis or tracheobronchitis, bronchiectasis, cystic fibrosis, asthma, tuberculosis, and fungal infections. For such therapies, a solution or finely divided dry preparation of the actin-resistant variant is instilled in conventional fashion into the airways (e.g., bronchi) or lungs of a patient, for example by aerosolization.

The actin-resistant variants are also useful for adjunctive treatment of abscesses or severe closed-space infections in conditions such as empyema, meningitis, abscess, peritonitis, sinusitis, otitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. The actin-resistant variant may improve the efficacy of antibiotics used in the treatment of such infections (e.g., gentamicin activity is markedly reduced by reversible binding to intact DNA).

Native human DNase I and actin-resistant variants thereof also may be useful for the treatment for systemic lupus erythematosus (SLE), a life-threatening autoimmune disease characterized by the production of diverse autoantibodies. DNA is a major antigenic component of the immune complexes. In this instance, the human DNase I (native or variant) may be given systemically, for example by intravenous, subcutaneous, intrathecal, or intramuscular administration to the affected patient.

Native human DNase I and actin-resistant variants thereof also may be useful for preventing the new development and/or exacerbation of respiratory infections, such as may occur in patients having cystic fibrosis, chronic bronchitis, asthma, pneumonia, or other pulmonary disease, or patients whose breathing is assisted by ventilator or other mechanical device, or other patients at risk of developing respiratory infections, for example post-surgical patients.

The actin-resistant variants can be formulated according to known methods to prepare therapeutically useful compositions. A preferred therapeutic composition is a solution of an actin-resistant variant in a buffered or unbuffered aqueous solution, and preferably is an isotonic salt solution such as 150 mM sodium chloride containing 1.0 mM calcium chloride at pH 7. These solutions are particularly adaptable for use in commercially-available nebulizers including jet nebulizers and ultrasonic nebulizers useful for administration directly into the airways or lungs of an affected patient.

In another embodiment, the therapeutic composition comprises a dry powder of the actin-resistant variant, preferably prepared by spray-drying of a solution of the actin-resistant variant, essentially as described in U.S. patent application Ser. No. 08/206,020 (filed Mar. 4, 1994).

In a further embodiment, the therapeutic composition comprises cells actively producing an actin-resistant variant of human DNase I. Such cells may be directly introduced into the tissue of a patient, or may be encapsulated within porous membranes which are then implanted in a patient, in either case providing for the delivery of the actin-resistant variant into areas within the body of the patient in need of increased concentrations of DNA-hydrolytic activity. For example, the patient's own cells could be transformed, either in vivo or ex vivo, with DNA encoding an actin-resistant variant of human DNase I, and then used to produce the DNase I directly within the patient.

The therapeutically effective amount of an actin-resistant human DNase I variant will depend, for example, upon the amount of DNA and actin in the material to be treated, the therapeutic objectives, the route of administration, and the condition of the patient. Accordingly, it will be necessary for the therapist to titer the dosage and modify the route of administration as required to obtain the optimal therapeutic effect. In view of its reduced binding affinity for actin and consequential increased DNA-hydrolytic activity in the presence of actin relative to native human DNase I, the amount of an actin-resistant variant required to achieve a therapeutic effect may be less than the amount of native human DNase I necessary to achieve the same effect under the same conditions. Generally, the therapeutically effective amount of the actin-resistant variant will be a dosage of from about 0.1 $\mu$g to about 5 mg of the variant per kilogram of body weight of the patient, administered within pharmaceutical compositions, as described herein.

An actin-resistant DNase I variant optionally is combined with or administered in concert with one or more other pharmacologic agents used to treat the conditions listed above, such as antibiotics, bronchodilators, anti-inflammatory agents, mucolytics (e.g. n-acetyl-cysteine)-, actin binding or actin severing proteins (e.g., gelsolin; Matsudaira et al., Cell 54:139–140 (1988); Stossel, et al., PCT Patent Publication No. WO 94/22465 (published Oct. 13, 1994)), protease inhibitors, or gene therapy product (e.g., comprising the cystic fibrosis transmembrane conductance regulator (CFTR) gene, Riordan, et al., Science 245:1066–1073 (1989)).

The following examples are offered by way of illustration only and are not intended to limit the invention in any manner. All patent and literature references cited herein are expressly incorporated.

EXAMPLE 1

Mutagenesis of Human DNase I

*E. coli* strain CJ236 (BioRad Laboratories, Richmond, California USA) was transformed with plasmid pRK.DNase.3 using the method of Chung et al. (Nuc. Acids. Res. 16:3580 (1988). The plasmid pRK.DNase.3 used in making the present invention is as described in PCT Patent Publication No. WO 90/07572 (published Jul. 12, 1990), except that the nucleotide sequence encoding human DNase I is as shown in FIG. 1. Transformed cells were plated on LB agar plates containing 50 μg/ml carbenicillin and grown overnight at 37° C. 2YT broth (5 ml) containing 50 μg/ml carbenicillin and 10 μl VCSM13 helper phage (Stratagene, La Jolla, Calif. USA) was inoculated with an individual colony from the agar plate and grown overnight at 37° C. with agitation. Single stranded DNA was isolated from this culture and used as template for subsequent mutagenesis.

Site-directed mutagenesis was accomplished using synthetic oligonucleotides according to the method of Kunkel, et al. (Meth. Enzymol. 154: 367–382 (1987). The mutagenic oligonucleotides were 21-mers or 24-mers, having either 9 or 12 exact base matches 5' to the mismatched codon and 9 exact base matches 3' to the mismatched codon. Following mutagenesis, single stranded DNA from individual clones was subjected to dideoxy sequencing (Sanger, et al., Proc. Nat. Acad. Sci. USA 74: 5463–5467 (1977)). DNA having variant nucleotide sequences then was transformed as described above into E. coli strain XL1 Blue MRF' (Stratagene). After plating and single colony isolation as before, individual colonies were used to inoculate 0.5 liter LB broth containing 50 ug/ml carbenicillin. Following growth overnight with agitation at 37° C., the cells were harvested by centrifugation and the variant DNA (in the expression vector) was purified using Qiagen tip-500 columns (Qiagen Inc., Chatsworth, Calif. USA).

FIGS. 2–6 identify the different human DNase I variants that were made. In the figures and throughout the specification, the description of the amino acid substitution mutation(s) present in a DNase I variant is abbreviated by a first alphabetical letter, a number, and a second alphabetical letter. The first alphabetical letter is the single letter abbreviation of amino acid residue in native (wild-type) human mature DNase I, the number indicates the position of that residue in native human mature DNase I (numbering as shown in FIG. 1), and the second alphabetical letter is the single letter abbreviation of the amino acid residue at that position in the variant DNase I. For example, in the DNase I variant having a D53R mutation, the aspartic acid (D) residue at position 53 in native human mature DNase I has been replaced by an arginine (R) residue. Multiple mutations in a single variant are designated similarly, with a colon (:) separating each of the different mutations that are present in the variant. For example, the designation D53R:Y65A indicates that the variant has a D53R mutation and a Y65A mutation.

EXAMPLE 2

Expression of Human DNase I Variants

Human embryonic kidney 293 cells (ATCC CRL 1573, American Type Culture Collection, Rockville, Md. USA) were grown in serum containing media in 150 mm plastic Petri dishes. Log phase cells were transiently cotransfected with 22.5 μg purified variant DNA (prepared as described above) and 17 μg adenovirus DNA using the calcium phosphate precipitation method (Gorman, et al., DNA and Protein Eng. Tech. 2:3–10 (1990)). Approximately 16 hours after transfection, the cells were washed with 15 ml phosphate buffered saline and the media was changed to serum free media. Two harvests of the cell culture media were taken from each plate, the first at either 24 or 72 hours and the last at 96 hours following the serum free media change. A total of approximately 50 ml of cell culture supernatant containing the DNase I variant was obtained in this way. The pool of culture supernatant collected from each plate was concentrated 5 to 50 fold using Centriprep 10 concentrators, and the concentrates were assayed to determine various biochemical and biological activities of the DNase I variants.

Concentrate containing native human DNase I was prepared by the same procedure as described above, except that the 293 cells were transiently transfected with plasmid pRK.DNase.3.

EXAMPLE 3

Biochemical and Biological Activities of Human DNase I Variants

I. Relative Specific Activity

The relative specific activity of DNase I variants was assessed by comparing the activity of the variant to that of native human DNase I in two different assays. In particular, the relative specific activity of the variants is defined as the concentration of the variant (in μg/ml) determined in a methyl green activity assay (Sinicropi, et al., Anal. Biochem. 222:351–358 (1994); Kurnick, Arch. Biochem. 29:41–53 (1950)) divided by the concentration of the variant (in μg/ml) determined in a DNase I ELISA assay (described below). In both the methyl green activity assay and the DNase I ELISA assay, the standard curves were determined using Pulmozyme® human DNase I. The relative specific activity of native human DNase I and variants are shown in FIGS. 2A–D.

The methyl green activity assay (Sinicropi, et al., Anal. Biochem. 222:351–358 (1994); Kurnick, Arch. Biochem. 29:41–53 (1950)) utilizes methyl green dye, which intercalates approximately every 10 bases in the DNA, resulting in a green substrate. As the DNA is cleaved by the DNase I, the methyl green dye is released and oxidized to a colorless form. Thus, the loss of green color is proportional to the amount of DNase I added to the assay sample. The amount of DNase I present in the assay is then quantitated by comparison to a standard curve that is prepared by assaying known quantities of DNase I.

The DNase I ELISA assay involves coating microtiter plates with a goat anti-DNase I polyclonal antibody, adding the sample to be assayed, and detecting any resulting bound DNase I with a rabbit anti-DNase I polyclonal antibody which is conjugated to horseradish peroxidase (HRP). When HRP substrate and color development reagent are added, the color developed is proportional to the amount of DNase I present in the sample. The amount of DNase I present in the assay is then quantitated by comparison to a standard curve that is prepared by assaying known quantities of DNase I.

In both assays, multiple dilutions of the samples were assayed and those values which fell in the mid-range of the standard curve were averaged and standard deviations calculated.

Also, the DNase I concentration as determined by the DNase I ELISA assay was used to standardize DNase I concentrations in other assays in which the DNase I variants were characterized (e.g., in assays of inhibition by actin, described below).

II. Actin Inhibition of DNase I Hydrolytic Activity

G-actin (Kabsch, et al., Ann. Rev. Biophys. Biomol. Struct. 21:49–76 (1992)) was prepared by dialyzing overnight a 1 mg/ml solution of actin (obtained either commercially (Sigma, St. Louis, Mo. USA) or prepared by the method of Pardee, et al., Meth. Enzymol. 85:164–181 (1982)) against 5 mM HEPES, pH 7.2, 0.2 mM $CaCl_2$, 0.5 mM ATP, 0.5 mM β-mercaptoethanol at 4° C. After centrifugation at 13,000×g for 5 min, the amount of G-actin was quantitated by measuring the absorbance at 290 nm; a 1 mg/ml solution has an absorbance of 0.66 OD. The amount of G-actin preparation required to substantially (>50% inhibition) but not totally inhibit the DNA-hydrolytic activity of native human DNase I was determined in preliminary experiments under the same conditions used for each assay.

Sensitivity to actin inhibition was assessed by measuring the DNA-hydrolytic activity of the variants in the presence and absence of actin in either of two different assays, the methyl green assay previously described and a hyperchromicity assay which is based on the increase in absorbance at 260 nm upon denaturation and depolymerization of DNA (Kunitz, J. Gen. Physiol. 33:349–35 362 (1950); Kunitz, J. Gen. Physiol. 33:363–377 (1950)). The percent inhibition of selected variants in these assays are shown in FIGS. 3 and 4.

In the hyperchromicity assay, concentrated culture supernatants (prepared as described above, containing DNase I variants) were incubated either with no added or a 2- to 3-fold molar excess of actin in buffer A (25 mM HEPES, pM 7.5, 4 mM $CaCl_2$, 4 mM $MgCl_2$, 0.1% BSA) for one hour at room temperature before being added to a cuvette containing 40 μg DNA in a total assay volume of 1.0 ml. The final concentration of the DNase I variant in the assay was approximately 26 nM, as determined by DNase I ELISA assay. The rates of DNA hydrolysis by the DNase I variants in the presence and absence of actin were measured. The percent activity shown in FIGS. 3 and 4 was calculated by determining the ratio of the DNA hydrolytic activity of the human DNase I (native or variant) in the presence of actin to its DNA-hydrolytic activity in the absence of actin and multiplying by 100.

In the methyl green assay, concentrated culture supernatants (prepared as described above, containing DNase I variants) were incubated either with no added actin or a 1000-fold molar excess of actin in buffer B (25 mM HEPES, pH 7.5, 4 mM $CaCl_2$, 4 mM $MgCl_2$, 0.1% BSA, 0.01% thimerosal, and 0.05% Tween 20) at 37° C. for 16 hours. The concentration of active enzyme in each case was estimated by comparison with the standard curve of Pulmozyme®. The "percent activity" remaining of the variant refers to the 100 times the ratio of the activity in the presence of actin to the activity in the absence of actin.

Figure 2A:
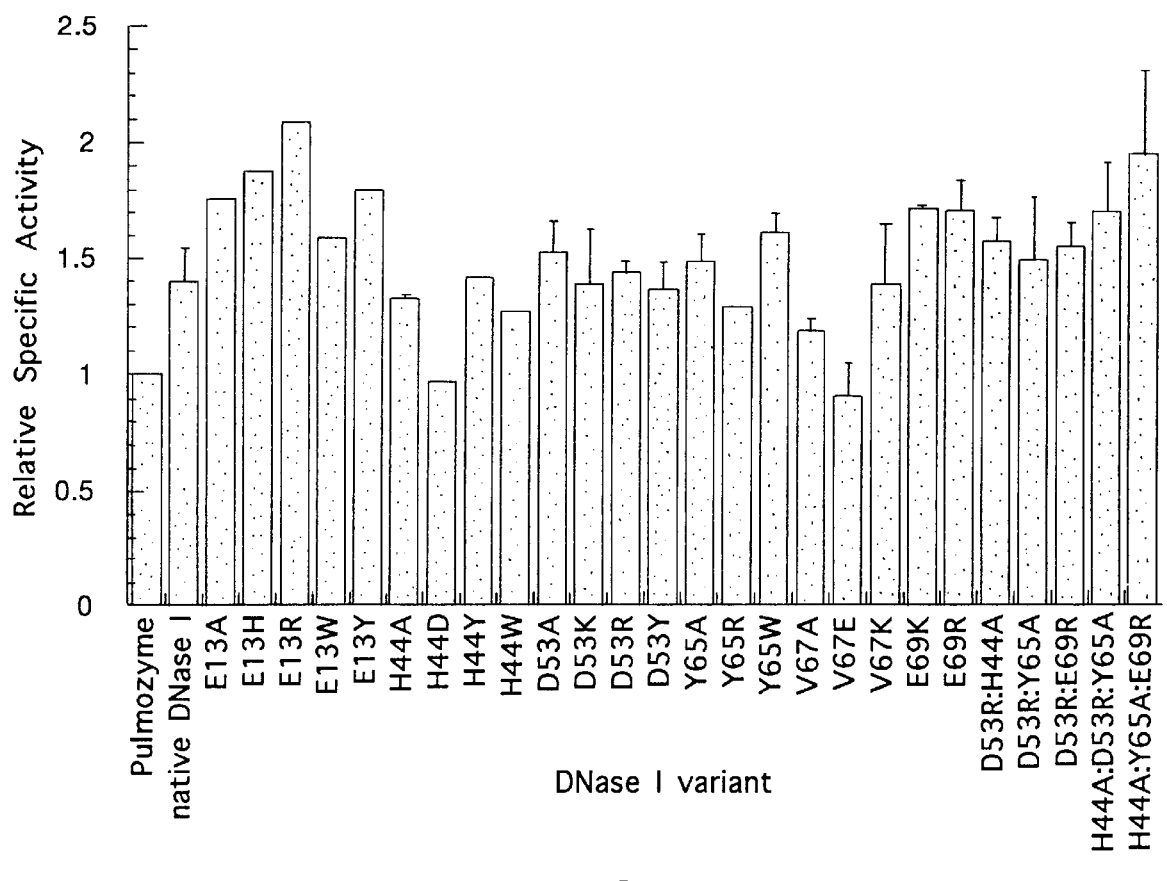
FIGS. 2A–D show the relative specific activity of native human DNase I and variants. The error bars represent the standard deviation (n-weighted). The relative specific activity of Pulmozyme® human DNase I (Genentech, Inc., South San Francisco, Calif. USA) is defined as 1.0. The relative specific activity of native human DNase I is greater than that of Pulmozyme® due to the occurrence in Pulmozyme® of a deamidated form of human DNase I that has reduced DNA-hydrolytic activity (Frenz, et al., PCT Patent Publication No. WO 93/25670, published Dec. 23, 1993).
Figure 2B:
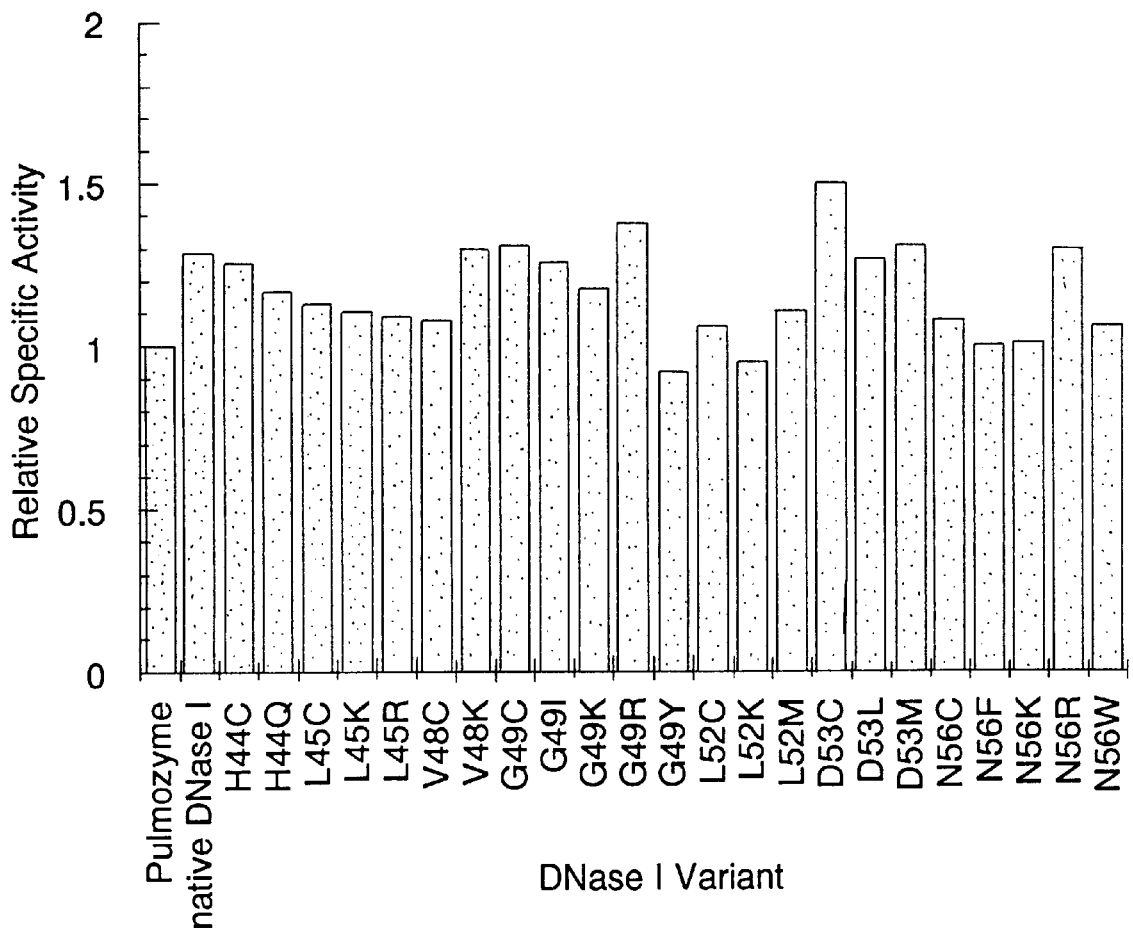
Figure 2C:
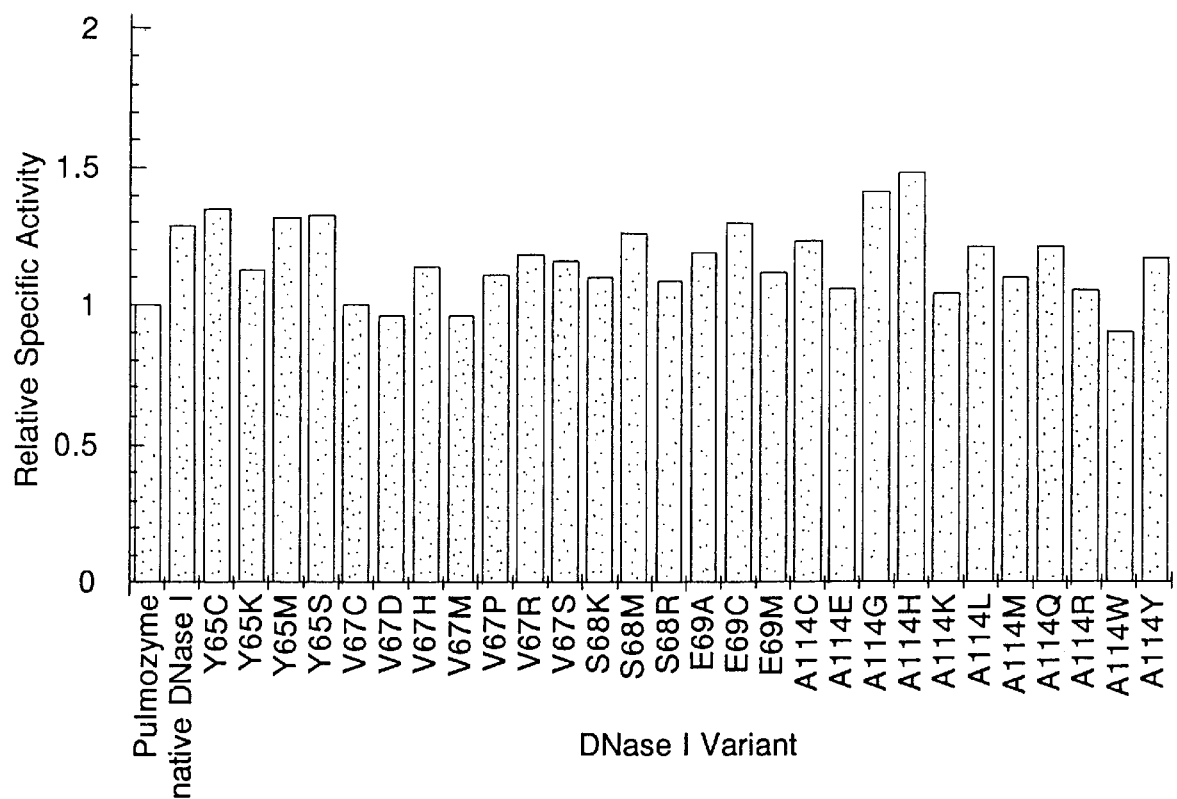
Figure 2D:
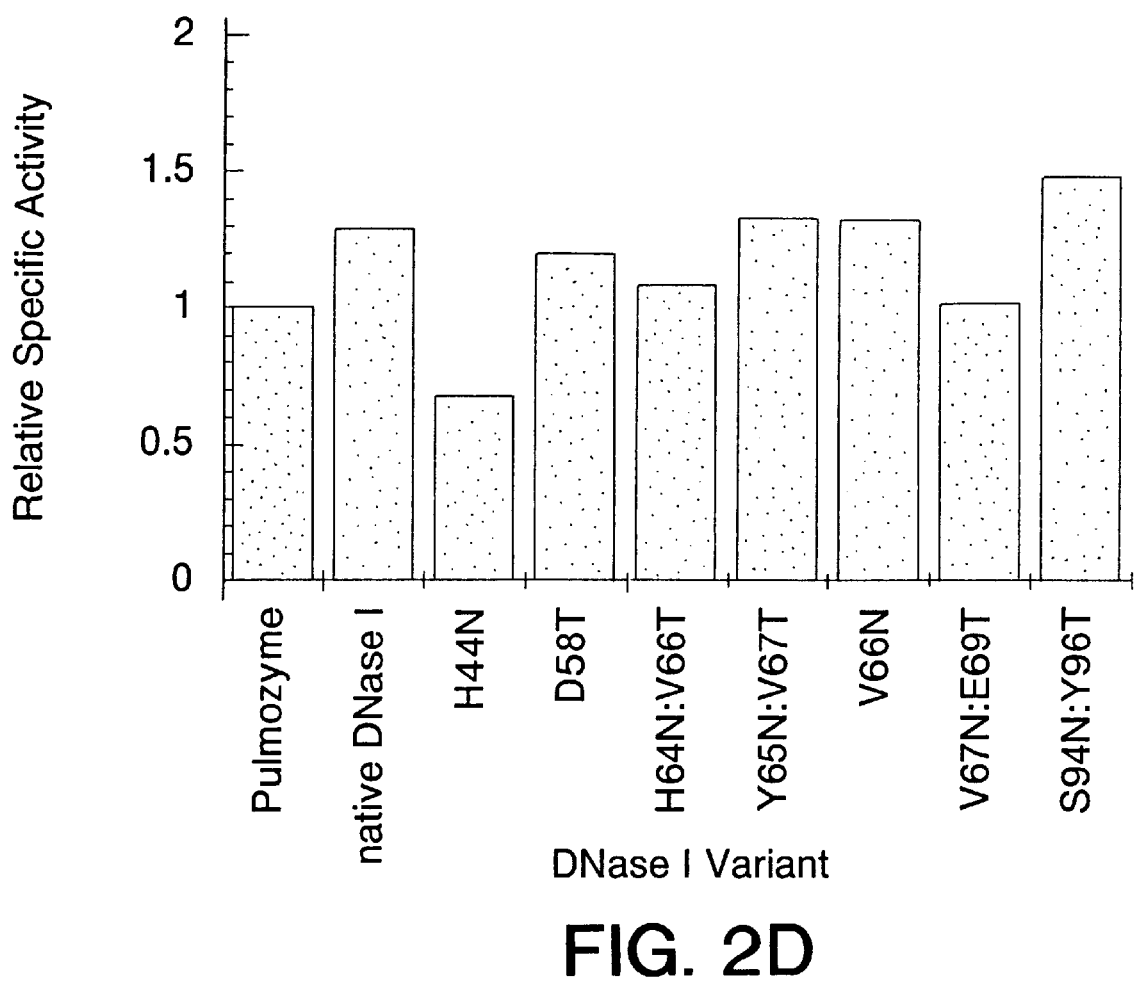
Figure 3:
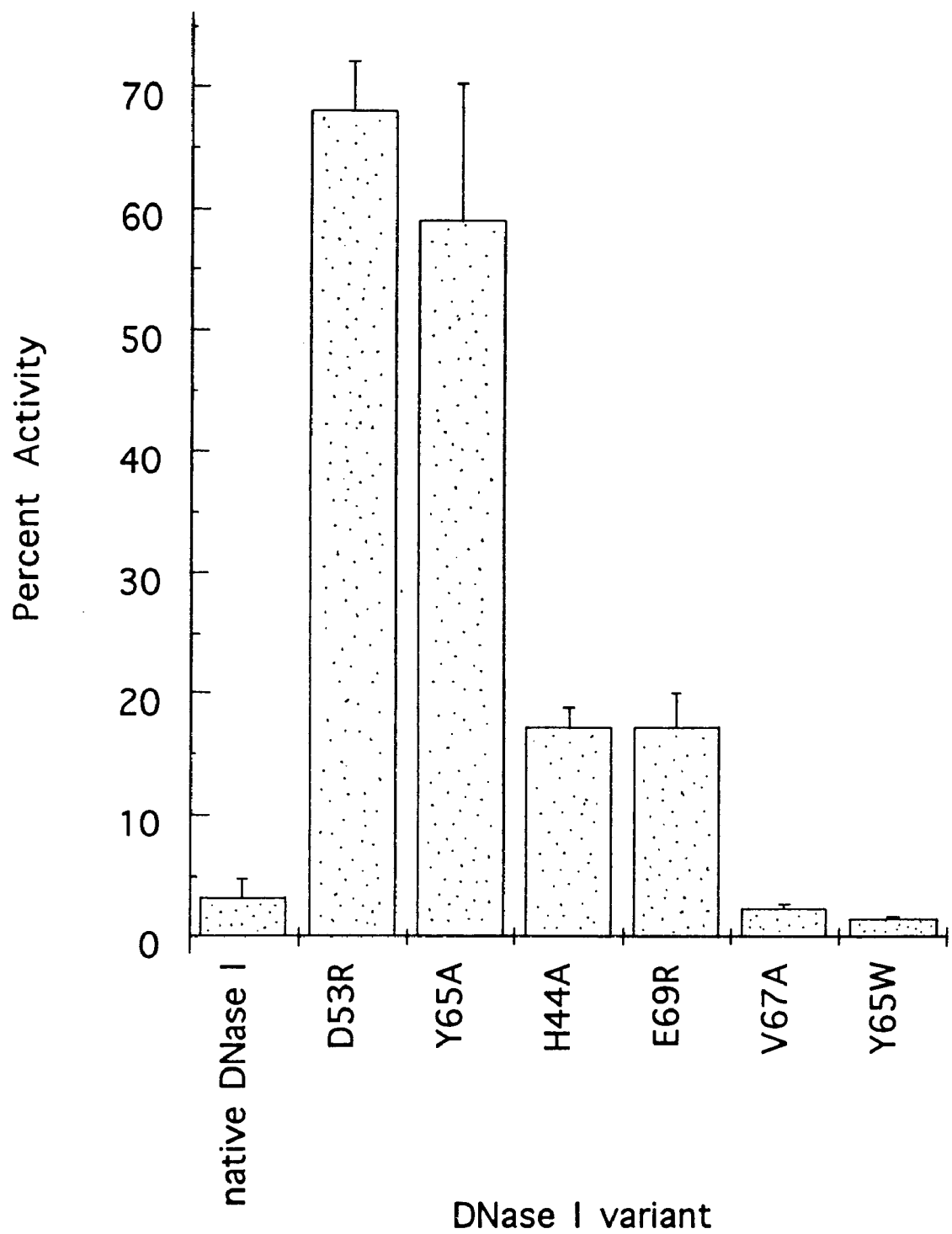
FIG. 3 shows the DNA-hydrolytic activity of native human DNase I and single-residue variants of human DNase I in the presence of actin, as determined in a hyperchromicity assay. "Percent activity" is the percent DNA-hydrolytic activity of the DNase I (native or variant) calculated as described in Example 3; the DNA-hydrolytic activity of the DNase I in the absence of actin is defined as 100 percent activity. The error bars represent the standard deviation.
Figure 4:
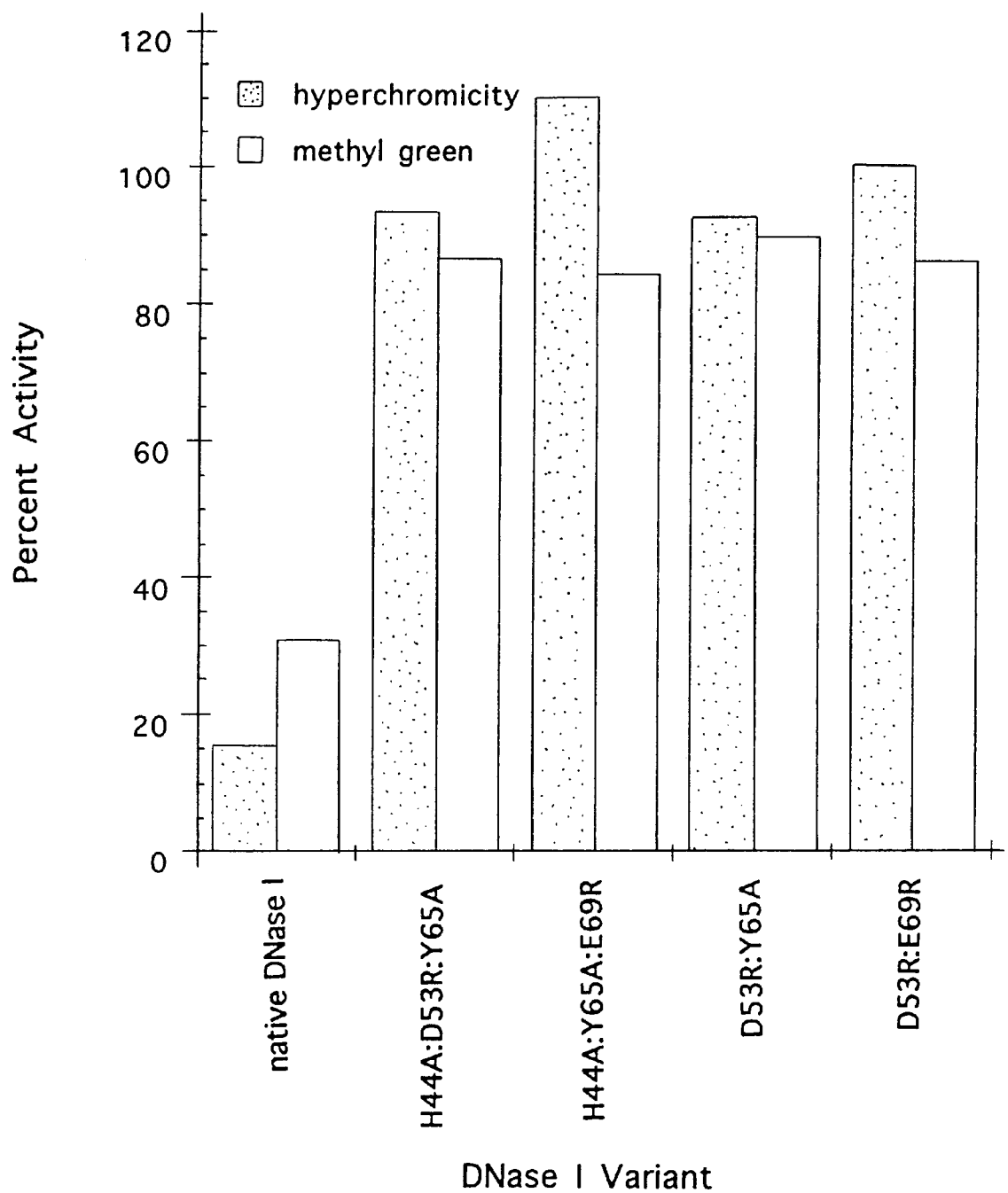
FIG. 4 shows the DNA-hydrolytic activity of native human DNase I and multiple-residue variants of human DNase I in the presence of actin, as determined in a hyperchromicity assay or a methyl green assay. "Percent activity" is the percent DNA-hydrolytic activity of the DNase I (native or variant) calculated as described in Example 3; the DNA-hydrolytic activity of the DNase I in the absence of actin is defined as 100 percent activity. The error bars represent the standard deviation.

As shown in FIGS. 3 and 4, the DNA-hydrolytic activity of native human DNase is substantially reduced in the presence of actin. By comparison, various single- and multiple-residue variants of native human DNase are relatively resistant to inhibition by actin, as indicated by their having greater DNA-hydrolytic activity in the presence of actin than native human DNase I.

III. Actin Binding ELISA

A microtiter based assay was developed to measure the binding of native human DNase I and DNase I variants to immobilized actin. First, the wells of a MaxiSorp plate (Nunc, Inc., Naperville, Ill., USA) were coated with 100 ul per well human GC globulin (Calbiochem, La Jolla, Calif. USA), an actin binding protein (Goldschmidt-Clermont, et al, Biochem. J. 228:471–477 (1985), McLeod, et al., J. Biol. Chem. 264:1260-1267 (1989), Houmeida, et al., Eur. J. Biochem. 203:499–503 (1992)), at a concentration of 10 ug/ml in 25 mM HEPES, 4 mM $MgCl_2$, 4 mM $CaC_2$, pH 7.2, at 4° C. for 16–24 hours. After discarding the GC globulin, excess reactive sites were blocked by the addition of 200 ul per well buffer C (buffer C is the same as buffer B, above, with the addition of 0.5 mM adenosine triphosphate; buffer C was used as the assay diluent in all subsequent steps unless otherwise noted) and incubating the plate on a shaker for 1–2 hours at room temperature. Each incubation step which follows was carried out at room temperature for one hour on a Mini Orbital Shaker (Bellco Biotechnology, Vineland, New Jersey USA); between each of the steps, the plate was emptied and washed 6 times with phosphate buffered saline containing 0.05% Tween 20 with a Microwash II plate washer (Skatron A/S, Norway). Next, G-actin, prepared as described above, was diluted to 50 ug/ml in buffer C and 100 ul was added to each well; the plates were incubated and washed, and 100 ul of various dilutions of Pulmozyme® and cell culture media containing either native human DNase I or variants thereof were added to the wells and the plates incubated and washed. Finally, 100 ul of a 1/25,000 dilution of an anti-human DNase I rabbit polyclonal antibody-horseradish peroxidase conjugate (original stock concentration was 465 ug/ml) was added to each well. After incubation and washing, color development was initiated by the addition of 100 ul per well color development reagent (Sigma Fast o-phenylenediamine and urea/$H_2$ $O_2$ tablets solubilized according to the manufacturer's recommendation) and stopped by the addition of 100 ul per well 4.5 N $H_2SO_4$. The absorbance at 492 nm was recorded and plotted versus the concentration of DNase I originally added to the well. Sigmoidal curves resulted for native human DNase I and those variants which bound to actin; these curves were fit to a four parameter equation by nonlinear regression analysis (Marquardt, J. Soc. Indust. Appl. Math. 11:431–441 (1963); the concentration of each DNase I (native or variant) required to give a half-maximal signal in the assay was calculated from the curves and is referred to as the $EC_{50}$ value. The molecular mass of native human DNase I and the variants was assumed to be 37,000 Daltons.

The relative binding affinity of each human DNase I variant was calculated by dividing the $EC_{50}$ value of the variant by the $EC_{50}$ value of native human DNase I determined in the ELISA assay, and the results are shown in FIGS. 5A–D. By way of example, if the relative binding affinity of the human DNase I variant were calculated to be 5, this value would indicate that the $EC_{50}$ value of the variant is 5-fold greater than the $EC_{50}$ value of native human DNase, or in other words, that the variant has an affinity for actin that is 5-fold less than the affinity of native human DNase I for actin in this ELISA assay.

IV. Sputum Compaction Assays

A sputum compaction assay (PCT Patent Publication No. WO 94/10567, published May 11, 1994) was used to measure the relative viscoelasticity of sputum from cystic fibrosis patients ("CF sputum") before and after incubation with native human DNase I and different DNase I variants. After mixing CF sputum with a DNase I sample and incubating for 20 min at room temperature, the semi-solid solutions were loaded into capillary tubes which then were centrifuged at 12,000 rpm for 20 minutes. Following centrifugation, the height of the pellet was measured and compared to the height of the solution plus pellet. These measurements were then used to calculate the percent compaction of the sputum, which correlates with the viscoelasticity of the sputum.

Figure 6:
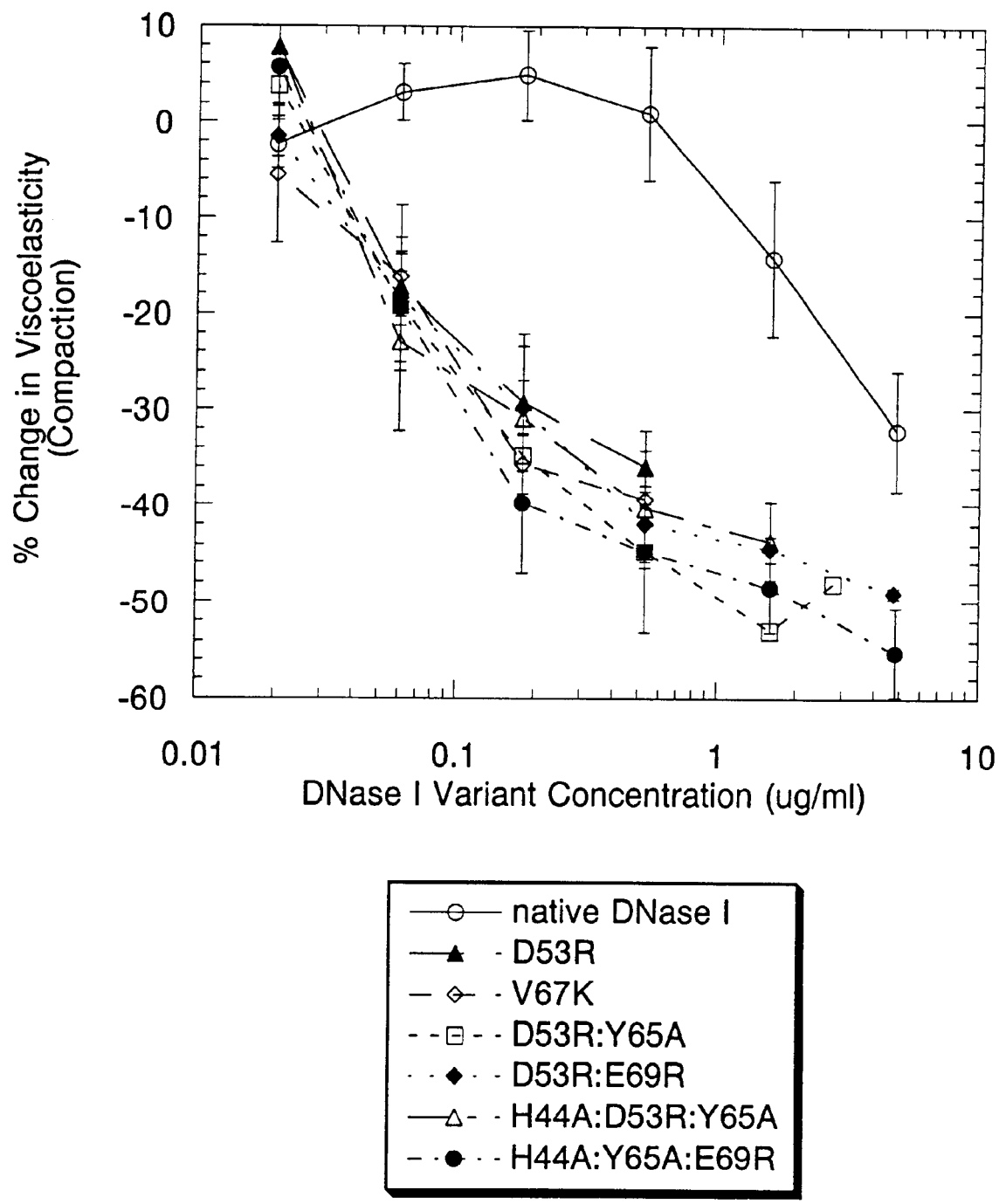
FIG. 6 shows the mucolytic activity of native human DNase I and variants of human DNase I in sputum samples from cystic fibrosis patients, as determined by a compaction assay. The error bars represent the standard error of the mean.
Figure 7:
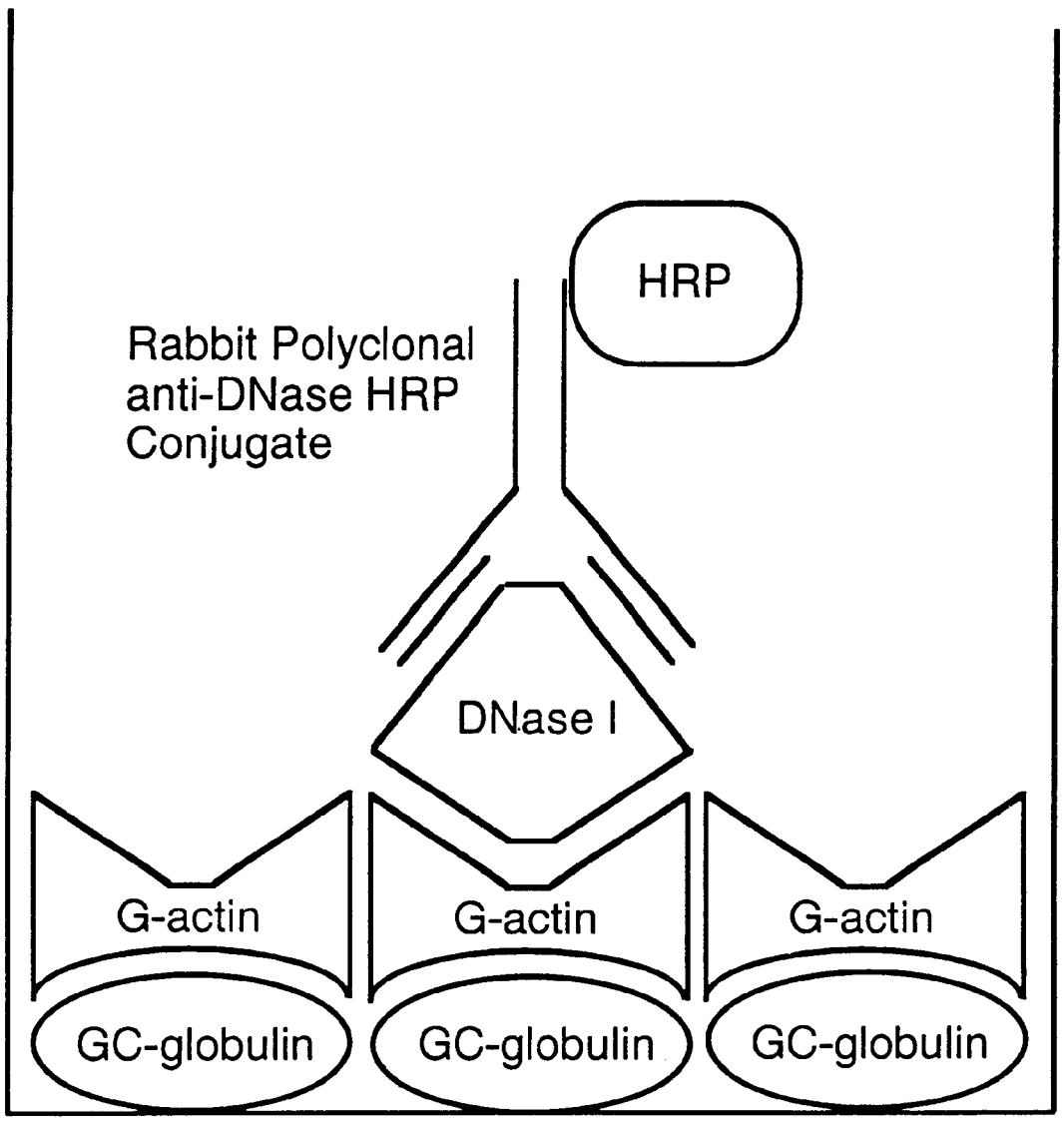
FIG. 7 shows a schematic representation of the actin binding ELISA assay described in Example 3.

The percent compaction determined upon treatment of CF sputum with native human DNase I and human DNase I actin-resistant variants is shown in FIG. 6. These results indicate that the human DNase I actin-resistant variants are more effective than native human DNase I in reducing the viscoelasticity of CF sputum, as determined by the compaction assay.

What is claimed is:

1. A variant of human DNase I (SEQ ID NO: 1) comprising at least one amino acid substitution at the following positions corresponding to the sequence of native human DNase I: His44, Leu45, Val48, Gly49, Leu52, Asp53, Asn56, His64, Tyr65, Val66, Val67, Ser68, Glu69, Ser94, Tyr96 or Ala 114, wherein said variant has DNA hydrolytic activity.

2. A variant of claim 1 that has a binding affinity for actin that is at least five-fold less than that of native human DNase I.

3. A variant of claim 1 that has a binding affinity for actin that is at least 100-fold less than that of native human DNase I.

4. A variant of claim I comprising an amino acid sequence having at least 90% identity with the amino acid sequence of native human DNase I (SEQ ID NO:1).

5. A variant of claim 1 comprising an amino acid sequence having at least 95% identity with the amino acid sequence of native human DNase I (SEQ ID NO: 1).

6. A variant of claim 1 having an amino acid sequence that differs from the amino acid sequence of native human DNase I (SEQ ID NO: 1) by the substitution of one amino acid for another at only a single position within the sequence.

7. An isolated nucleic acid encoding a human DNase I variant according to claim 1.

8. The nucleic acid of claim 7 comprising a nucleotide sequence that encodes an amino acid sequence having at least 90% identity with the amino acid sequence of native human DNase I (SEQ ID NO: 1).

9. The nucleic acid of claim 7 comprising a nucleotide sequence that encodes an amino acid sequence having at least 95% identity with the amino acid sequence of native human DNase I (SEQ ID NO: 1).

10. The nucleic acid of claim 7 comprising a nucleotide sequence that encodes an amino acid sequence that differs from the amino acid sequence of native human DNase I (SEQ ID NO: 1) by the substitution of one amino acid for another at only a single position within the sequence.

11. A method of the treatment of a patient having a pulmonary disease or disorder comprising administering to the patient a therapeutically effective amount of a variant of human DNase I according to claim 1.

12. The method of claim 11 wherein the disease or disorder is cystic fibrosis.

13. The method of claim 11 wherein the disease or disorder is chronic bronchitis.

14. A pharmaceutical composition comprising a variant of human DNase I according to claim 1 and a pharmaceutically acceptable excipient.

15. The composition of claim 14 wherein the composition is in liquid form.

16. The composition of claim 15 wherein the composition is in powder form.

17. A variant of a human DNase I (SEQ ID NO: 1) comprising at least one amino acid substitution selected from the group consisting of E13A, E13H, E13R, E13W, E13Y, H44A, H44D, H44Y, H44W, H44C, H44Q, H44N, H44E, L45C, L45K, L45R, V48C, V48K, V48R, G49C, G49I, G49K, G49R, G49Y, L52C, L52K, L52M, L52N, L52R, D53A, D53K, D53R, D53Y, D53C, D53L, D53M, N56C, N56F, N56K, N56R, N56W, D58T, H64N, Y65A, Y65R, Y65W, Y65C, Y65K, Y65M, Y65S, Y65N, Y65E, Y65P, V66T, V66N, V67A, V67E, V67K, V67C, V67D, V67H, V67M, V67P, V67R, V67S, V67T, V67N, S68K, S68R, S68M, S68N, E69K, E69R, E69A, E69C, E69M, E69T, P70T, S94N, Y96T, A114C, A114E, A114G, A114H, A114K, A114L, A114M, A114Q, A114R, A114W and A114Y, wherein said variant has DNA hydrolytic activity.

18. A variant according to claim 17, comprising at least one amino acid substitution selected from the group consisting of: E13A, E13H, E13R, E13W, E13Y, H44A, G49R, D53R, D53K, D53Y, D53A, D53C, N56R, Y65A, Y65R, Y65W, V67E, E69K, E69R A114G and A114H.

19. A variant according to claim 17, comprising at least one amino acid substitution selected from the group consisting of: H44A:D53R:Y65A, H44A:Y65A:E69R, D53R:Y65A, D53R:E69R, S94N:Y96T, V67N:E69T, Y65N:V67T and H64N:V66T.

20. A variant of claim 17 comprising an amino acid sequence having at least 90% identity with the amino acid sequence of native human DNase I (SEQ ID NO: 1).

21. A variant of claim 17 comprising an amino acid sequence having at least 95% identity with the amino acid sequence of native human DNase I (SEQ ID NO: 1).

* * * * *